(12) United States Patent
Donnangelo

(10) Patent No.: US 7,330,032 B2
(45) Date of Patent: Feb. 12, 2008

(54) TECHNIQUES FOR BUILDING-SCALE ELECTROSTATIC TOMOGRAPHY

(75) Inventor: Nicholas C. Donnangelo, Purcellville, VA (US)

(73) Assignee: The Mitre Corporation, McLean, VA (US)

(*) Notice: Subject to any disclaimer, the term of this patent is extended or adjusted under 35 U.S.C. 154(b) by 333 days.

(21) Appl. No.: 10/993,421

(22) Filed: Nov. 22, 2004

(65) Prior Publication Data
US 2005/0167588 A1    Aug. 4, 2005

Related U.S. Application Data

(60) Provisional application No. 60/533,077, filed on Dec. 30, 2003.

(51) Int. Cl.
*G01N 27/60* (2006.01)

(52) U.S. Cl. ............... 324/452; 324/457; 324/671

(58) Field of Classification Search ............ 324/452, 324/671, 674, 681, 682, 67, 662
See application file for complete search history.

(56) References Cited

U.S. PATENT DOCUMENTS

| | | | |
|---|---|---|---|
| 3,859,576 A | | 1/1975 | Sheckler et al. |
| 4,755,944 A | * | 7/1988 | Glass ............... 702/7 |
| 4,792,804 A | | 12/1988 | Rubechini |
| 4,833,698 A | | 5/1989 | Flannery et al. |
| 5,048,029 A | * | 9/1991 | Skupsky et al. ......... 372/26 |
| 5,172,110 A | | 12/1992 | Tiefengraber |
| 5,184,624 A | | 2/1993 | Brown et al. |
| 5,206,640 A | | 4/1993 | Hirvonen et al. |
| 5,252,912 A | | 10/1993 | Merritt et al. |
| 5,284,142 A | | 2/1994 | Goble et al. |
| 5,311,878 A | | 5/1994 | Brown et al. |
| 5,351,697 A | | 10/1994 | Cheney et al. |
| 5,381,333 A | | 1/1995 | Isaacson et al. |

(Continued)

FOREIGN PATENT DOCUMENTS

EP    0 075 199 A1    3/1983

OTHER PUBLICATIONS

English Abstract for European Patent Publication No. EP 0075199, 1 page, data supplied from espacenet.com.

(Continued)

*Primary Examiner*—Anjan Deb
(74) *Attorney, Agent, or Firm*—Sterne, Kessler, Goldstein & Fox, P.L.L.C.

(57) ABSTRACT

Techniques for imaging a search region to detect a dielectric target include placing multiple electrodes outside the search region. At least two electrodes are activated independently of each other. Emitter circuits are connected to corresponding emitter electrodes. Each emitter circuit is configured for using its emitter electrode to produce an electric field with wavelength longer than about one hundred meters. Receiver circuits are connected to corresponding receiver electrodes. Each receiver circuit is configured for using its receiver electrode to measure a property of an electric field produced, at least in part, by an emitter electrode. A processor determines a property of a dielectric target inside the search region based on measurements from the receiver circuits using a subset of the emitter circuits. Among other uses, these techniques allow humans to be detected inside building-size regions, even when hidden by visually opaque blocking material of small dielectric constant.

29 Claims, 15 Drawing Sheets

U.S. PATENT DOCUMENTS

| | | | |
|---|---|---|---|
| 5,421,345 | A | 6/1995 | Lekholm et al. |
| 5,430,381 | A * | 7/1995 | Dower ................... 324/452 |
| 5,446,461 | A | 8/1995 | Frazier |
| 5,455,590 | A | 10/1995 | Collins et al. |
| 5,465,730 | A | 11/1995 | Zadehkoochak et al. |
| 5,544,662 | A | 8/1996 | Saulnier et al. |
| 5,557,283 | A | 9/1996 | Sheen et al. |
| 5,588,429 | A | 12/1996 | Isaacson et al. |
| 5,610,517 | A | 3/1997 | Ma et al. |
| 5,626,146 | A | 5/1997 | Barber et al. |
| 5,641,965 | A | 6/1997 | Barber et al. |
| 5,651,955 | A | 7/1997 | Klaveness |
| 5,661,406 | A | 8/1997 | Daily et al. |
| 5,746,214 | A | 5/1998 | Brown et al. |
| 5,807,251 | A | 9/1998 | Wang et al. |
| 5,844,415 | A | 12/1998 | Gershenfeld et al. |
| 5,859,609 | A | 1/1999 | Sheen et al. |
| 5,865,754 | A | 2/1999 | Sevick-Muraca et al. |
| 5,914,610 | A | 6/1999 | Gershenfeld et al. |
| 5,919,142 | A | 7/1999 | Boone et al. |
| 5,936,412 | A | 8/1999 | Gershenfeld et al. |
| 6,015,389 | A | 1/2000 | Brown |
| 6,025,726 | A * | 2/2000 | Gershenfeld et al. ....... 324/671 |
| 6,026,173 | A | 2/2000 | Svenson et al. |
| 6,031,482 | A | 2/2000 | Lemaitre et al. |
| 6,051,981 | A | 4/2000 | Gershenfeld et al. |
| 6,066,954 | A | 5/2000 | Gershenfeld et al. |
| 6,147,497 | A | 11/2000 | Berryman et al. |
| 6,177,903 | B1 | 1/2001 | Fullerton et al. |
| 6,198,271 | B1 | 3/2001 | Heger et al. |
| 6,208,288 | B1 | 3/2001 | Shoucri et al. |
| 6,216,540 | B1 | 4/2001 | Nelson et al. |
| 6,218,846 | B1 | 4/2001 | Ludwig et al. |
| 6,263,096 | B1 | 7/2001 | Boag et al. |
| 6,308,097 | B1 | 10/2001 | Pearlman |
| 6,331,778 | B1 | 12/2001 | Daily et al. |
| 6,332,035 | B1 | 12/2001 | Basu et al. |
| 6,332,087 | B1 | 12/2001 | Svenson et al. |
| 6,336,045 | B1 | 1/2002 | Brooks |
| 6,366,232 | B1 | 4/2002 | Liedtke et al. |
| 6,392,692 | B1 | 5/2002 | Monroe |
| 6,400,307 | B2 | 6/2002 | Fullerton et al. |
| 6,404,377 | B1 | 6/2002 | Lee et al. |
| 6,408,043 | B1 | 6/2002 | Hu et al. |
| 6,417,797 | B1 | 7/2002 | Cousins et al. |
| 6,429,805 | B1 | 8/2002 | Cornic et al. |
| 6,445,810 | B2 | 9/2002 | Darrell et al. |
| 6,577,700 | B1 | 6/2003 | Fan et al. |
| 6,822,443 | B1 * | 11/2004 | Dogaru ................... 324/235 |
| 6,850,862 | B1 * | 2/2005 | Chidichimo et al. ........ 702/130 |
| 7,106,072 | B2 * | 9/2006 | Clauss et al. ............... 324/662 |
| 2001/0000025 | A1 | 3/2001 | Darrell et al. |
| 2001/0035837 | A1 | 11/2001 | Fullerton et al. |
| 2002/0008655 | A1 | 1/2002 | Haj-Yousef |
| 2002/0038096 | A1 | 3/2002 | Gregory et al. |
| 2002/0158790 | A1 | 10/2002 | Fullerton et al. |
| 2002/0175996 | A1 | 11/2002 | Porter et al. |
| 2003/0020629 | A1 | 1/2003 | Swartz et al. |
| 2004/0119633 | A1 | 6/2004 | Oswald et al. |
| 2004/0239305 | A1 * | 12/2004 | Clauss et al. ................. 324/67 |
| 2006/0254358 | A1 * | 11/2006 | Merkel ........................ 73/596 |
| 2007/0035437 | A1 * | 2/2007 | Steinway et al. ............. 342/22 |
| 2007/0208460 | A1 * | 9/2007 | Pienta et al. ................. 700/276 |

OTHER PUBLICATIONS

Cui, X., "The visualization of electric force lines in two-dimensional electric field computation," *Engineering Computations*, vol. 17, No. 2, pp. 166-174 (2000).

*Electric Field Disturbance Monitor*, at http://www.imagineeringezine.com/e-zine/efield.html, 6 pages (last updated Mar. 27, 2002).

Hibbs, A.D. et al., *Development and Test of Free Space Electric Field Sensors with Microvolt Sensitivity (U)*, 16 pages of PowerPoint Slides, date unknown.

Johnson, D., *Electric Field Disturbance Monitor Circuit Schematic*, 2 pages (Mar. 26, 2002).

*Electric and Magnetic Fields*, at http://www.hsph.harvard.edu/Organizations/Canprevent/emf.html, 7 pages (Copyright 1996).

*Electric Field Disturbance Monitor Materials List Rev A Feb. 10, 1999*, at http://www.imagineeringezine.com/e-zine/mat-list.html, 2 pages (printed Apr. 18, 2002).

Fong, A. et al., "Measurements and Analysis," *Reference Data for Engineers*, 8th Edition, pp. 12-1-12-13 (1993).

Gabriel, C. et al., "The dielectric properties of biological tissues: I. Literature survey," *Physics in Medicine & Biology*, vol. 41, pp. 2231-2249 (1996).

Gabriel, C. et al., "The dielectric properties of biological tissues: II. Measurements in the frequency range 10 Hz to 20 GHz," *Physics in Medicine & Biology*, vol. 41, pp. 2251-2269 (1996).

Gabriel, C. et al., "The dielectric properties of biological tissues: III. Parametric models for the dielectric spectrum of tissues," *Physics in Medicine & Biology*, vol. 41, pp. 2271-2293 (1996).

Jinno, K. et al., *Occupant Sensing Utilizing Perturbation of Electric Fields*, SAE Technical Paper Series, Paper No. 971051, ISSN No. 0148-7191, pp. 117-129 (1997).

Krupka, M.A. et al., *Development and Test of Free Space Electric Field Sensors with Microvolt Sensitivity*, Technical Report AD-A409234, 10 pages (Sep. 2001).

Mazzola, M.S. et al., "Gallium-Arsenide Optically Isolated Electric Field Sensor for Utility and Pulsed Power Applications," *Digest of Technical Papers: Tenth IEEE International Pulsed Power Conference*, pp. 372-377 (Jul. 3-6, 1995).

O'Brien, C.J., *Electric Field Sensors for Non Contact Graphical Interfaces*, Department of Information Technology and Electrical Engineering, University of Queensland, Thesis, 66 pages (Oct. 2001) and related summary, 3 pages.

Philipp, H., "The Charge Transfer Sensor," *Sensors*, pp. 36-40 & 42 (Nov. 1996).

*Remote Electric Field Sensor*, at http://www.llnl.gov/sensor_technology/STR14.html, 2 pages (last modified Aug. 16, 1995).

Scharfetter, H. et al., "Sensitivity maps for low-contrast perturbations within conducting background in magnetic induction tomography," *Physiological Measurement*, vol. 23, pp. 195-202 (2002).

Smith, J.R. et al., "Code Division Multiplexing of a Sensor Channel: A Software Implementation," *IEEE Journal On Selected Areas In Communications*, vol. 17, No. 4, pp. 725-731 (Apr. 1999).

Smith, J.R., "Distributed Protocols for ID Assignment," *Proceedings of the First Workshop on Automatic Identification Advanced Technologies*, Stony Brook, N.Y., 13 pages (Nov. 1997).

Smith, J., "Electric Field Sensing for Graphical Interfaces," *IEEE Computer Graphics and Applications*, pp. 54-60 (May/Jun. 1998).

Smith, J.R., "Field mice: Extracting hand geometry from electric field measurements," *IBM Systems Journal*, vol. 35, Nos. 3&4, pp. 587-608 (1996).

*The Swiss Cheese Imaging Algorithm*, at http://web.media.mit.edu/~irs/imaging/swisscheez.html, 2 pages (printed Apr. 8, 2002).

Zimmerman, T.G., *Applying Electric Field Sensing to Human-Computer Interfaces*, at http://www.acm.org/sigchi/chi95/Electronic/documnts/papers/tgz_bdy.htm, 8 pages (printed Apr. 5, 2002).

*Standard Handbook for Electrical Engineers*, 12th Edition, pp. 3-57-3-65 (1987).

*Notification of Transmittal of the International Search Report and the Written Opinion of the International Searching Authority, or the Declaration*, from PCT Appl. No. PCT/US04/38875, filed Nov. 22, 2004, 14 pages.

\* cited by examiner

TECHNIQUES FOR BUILDING-SCALE ELECTROSTATIC TOMOGRAPHY

CROSS-REFERENCE TO RELATED APPLICATIONS

This application claims benefit under 35 U.S.C. §119(e) to Provisional Patent Application No. 60/533,077, filed Dec. 30, 2003, which is incorporated herein by reference in its entirety.

STATEMENT REGARDING FEDERALLY-SPONSORED RESEARCH AND DEVELOPMENT

Statement under MPEP 310. The U.S. government has a paid-up license in this invention and the right in limited circumstances to require the patent owner to license others on reasonable terms as provided for by the terms of contract No. DAAB07-03-C-N206, awarded by the Defense Advanced Research Projects Agency, the central research and development organization for the Department of Defense.

STATEMENT OF GOVERNMENTAL INTEREST

This invention was made in part with Government support under Contract No. DAAB07-03-C-N206 awarded by the Defense Advanced Research Projects Agency (DARPA) Advanced Technology Office (ATO). The Government has certain rights in the invention.

BACKGROUND OF THE INVENTION

1. Field of the Invention

The present invention relates to electrostatic tomography.

2. Description of the Related Art

Many operations involve searching for human activity where the humans do not communicate and cannot be readily seen. For example, rescuers search for survivors in building rubble or in landslides caused by earthquakes, floods, and combat. As another example, tactical units for armed services and police have a need for information on a number or deployment of concealed hostile forces and if the concealed forces possess weapons, such as small arms, or some combination of this information. These hostile persons can be concealed within a building, a building complex, an extent of forest, an expanse of shrubs, or the like.

Unfortunately, very few sensor technologies effectively image the interior of building structures or densely foliated expanses. Infrared, acoustic and radiation systems are often ineffective.

Infrared sensors measure thermal radiation. Most building and earthen structures provide high thermal impedance, i.e., resistance to the flow of heat. Building material is often selected for its high thermal impedance to provide the thermal insulation property that is a basic function of many human shelters. High thermal impedance retards the flow of heat from humans touching the interior surface of exterior walls, through the exterior walls, to the exterior surface where hot spots can be detected by infrared sensors. Thus, infrared sensors are ineffective where the humans are in interior chambers, or are deeply buried, or in circumstances where humans, who are in contact with the inside surfaces of exterior walls, are also moving.

Acoustic sensors are ineffective for similar reasons. Most earthen or building structures also provide high acoustic impedance, which channels or dampens acoustic signals, or both. Thus, acoustic sensors are often ineffective, where the humans are in interior chambers, or are deeply buried.

Radiation systems are ineffective for several reasons. For example, high frequency electromagnetic radiation used in RADAR (radio detection and ranging) systems do not effectively penetrate buildings. Very high frequency, high energy radiation, such as X-ray systems, gamma ray systems, and neutron systems either penetrate the humans of interest nearly as effectively as the walls, giving very low contrast signals that are difficult or expensive to process, or produce so much ionizing activity so as to be harmful to the humans being detected. A system that injures the humans to be detected renders the system useless for search and rescue, for discriminating friendly forces from hostile forces or for situations, such as in an urban surrounding, where non-combatants may be exposed to excessive levels of ionizing radiation.

Similar concerns apply where the targets of interest are other biological entities, such as animals used for guard or attack purposes or contraband animals subject to illegal trade.

Low frequency electric fields with long wavelengths are known to penetrate various materials to distances related to their wavelengths and are known to be affected by the electrical properties of the material penetrated. (See, for example, Scharfetter H, Riu P, Populo M, Rosell J., "Sensitivity maps for low-contrast-perturbations within conducting background in magnetic induction tomography (MIT)," *Physiol Meas*, vol. 23: p195-202, 2002, which is incorporated by reference herein in its entirety). Within such distances, the electric fields can be considered "electrostatic" fields, and are so called hereinafter. In some references, such fields are sometimes called "quasi-electrostatic" fields.

Some techniques are known for inferring the distribution of electrical properties inside a region from electrostatic properties measured on a boundary of the region. These techniques are called hereinafter, "electrostatic tomography" techniques.

Measurements of electric field perturbation are used in a number of applications that do not require inversion using tomographic techniques. For example, electric wall stud locaters use a type of electric field measurement to sense differences in electrical capacitance to distinguish wood from air or insulation a few centimeters behind plasterboard. These single pole measurement devices do not estimate location or electrical properties of hidden materials, but merely detect changes in those electrical properties. In electric field intrusion detection systems, changes in electric fields are used to indicate the presence of an intruder by disruption in an electric field, but these systems do not use a plurality of independent measurements to estimate in three dimensions (3-D) the location or other properties of the intruder.

Intrusion systems are point sensors or netted point sensors. Their measurement data lacks the spatial and geometric information required for a tomographic inversion to reconstruct an image based on the intruder and surrounding space. Hence, the output of capacitance intrusion sensors is an indication that an intruder has perturbed the field at a particular location, usually by direct contact with the field or being in very close proximity to the field. For example, one form of capacitance based intrusion detection system uses a series of wires strung along a perimeter. When a conducting object, such as a person, approaches the wire assembly, some of the field lines emitted by the current carrying wire are intercepted by the proximate conductor and directed or shunted to ground, causing a corresponding decrease in the current measured in the sense wire. Localization of the disturbance may be accomplished by using time domain techniques widely known in the art. There is no practically feasible way a system like this could be used to distinguish proximate intruders from other conducting objects.

Another use of proximate electric field imaging disclosed in the literature involves detecting occupant proximity to seats for activating air bags and for child safety seats (see Gershenfeld et al U.S. Pat. No. 6,066,954 and Jinno, K., Ofuji, M., Asito T., and Sekido S. "Occupant Sensing Utilizing Perturbation of Electric Fields," in *Anthropomorphic Dummies and Crash Instrumentation Sensors* (SP-1361), Society of Automotive Engineers (SAE), Warrendale, PA, pp 117-129, 1997, which are incorporate by reference herein in their entireties).

There are four principal approaches to electrostatic tomography currently practiced, distinguished by the property mapped inside the region:

1) electrical capacitance tomography (ECT) maps electrical permittivity;

2) electrical impedance tomography (EIT) maps electrical impedance;

3) electo-magnetic tomography (EMT) maps magnetic permeability; and 4) electric field tomography (EFT) maps displacement currents induced in a conductor.

ECT has been used to determine properties of fluid flow through pipes. The capacitance is measured between two or more electrodes attached to opposite sides of the pipe. These systems typically require electrical contact between the sensor electrodes and the item for which capacitance is to be measured. Such a system is described, for example, in U.S. Pat. No. 6,577,700 B1 to L. Fan and W. Warsito (hereinafter Fan), which issued Jun. 10, 2003, which is incorporated herein by reference in its entirety. These systems rely on the dielectric properties of the material flowing in the pipe to develop an approximate space-time distribution. These systems do not detect, locate or characterize target objects, including biological organisms, cached in a large structure, such as a building.

Electrical impedance tomography (EIT) has been used in medical applications, for example to determine, non-invasively, broken bones within flesh. Such systems involve electrical contact between sensors and the flesh surrounding the bone. Such systems have been applied only over distances from a few to a few tens of centimeters and rely on measurement of conductivity and not capacitance through living tissue. These systems do not detect, locate or characterize target objects, including biological organisms, cached in a large structure, such as a building.

Similarly, electro-magnetic tomography (EMT) applications involve sensor electrodes in contact with the subject and ranges of tens of centimeters for computing an approximate 3-D distribution of neuronal activity within a human brain from extra-cranial measurements of electric potential (EEG) and/or magnetic field (MEG). EMT produces a blurred-localized image of a point source resulting in a low-resolution image of brain activity during epileptic spike and other neurological events. EMT systems presuppose electrode contact with the scalp and exploit passive electromagnetic emissions from the brain. They use only receiving electrodes, not emitting electrodes. These systems do not detect, locate or characterize target objects, including biological organisms, cached in a large structure, such as a building.

Electric Field Tomography (EFT) uses measurements of electrical potential or displacement currents induced by changes in electrical potential to reconstruct the location, size, shape and orientation of proximate conducting objects. Some EFT systems are directed to measure relative position and orientation of a human hand for use as a computer interface device. Such systems are described in U.S. Pat. No. 5,844,415 to Neil Gershenfeld and Joshua R. Smith, which issued Dec. 1, 1998 (hereinafter Gershenfeld I); U.S. Pat. No. 5,914,610 to Neil Gershenfeld and Joshua R. Smith, which issued Jun. 22, 1999 (hereinafter Gershenfeld II); and U.S. Pat. No. 5,936,412 to Neil Gershenfeld and Joshua R. Smith, which issued Aug. 10, 1999 (hereinafter Gershenfeld III), which are all incorporate herein by reference in their entireties. These systems use EFT over distances within a room and used fixed geometries for sensor placement. These systems are not suggested for circumstances of concern in the present invention, such as detecting humans concealed behind blocking material, like building structures or wooded areas, over distances on the scale of a building (e.g., about 5 m and more) when there is no access to the space being measured for placement of sensors.

Some electric field systems are directed to geo-prospecting by mapping perturbations in electric fields injected into the ground over wide geographic areas. These systems equate discontinuities in spatially separated measurements with inhomogeneities in the sub-surface geographic features that could be indicative of subterranean petroleum pockets. These systems are not properly called tomographic in that there is no computation of the inverse, as described in more detail in a later section.

One notional system (U.S. Pat. No. 5,206,640 to Esko Hirvonen and Juhani Ninivaara issued Apr. 27, 1993, which is incorporated by reference herein in its entirety) suggests using electrostatic fields to detect vessels, such as submarines, in narrow seaways, like straits and harbors. This system detects vessels as changes in measured currents due to conductivity differences between the vessel and seawater. However, this system relies on sensors that are embedded in the same conducting medium as the target, i.e., seawater, and that have fixed, unchanging geometries within the space being monitored. This system is not suggested for circumstances of concern in the present invention, such as detecting humans embedded in a non-conducting medium (air) and concealed behind non-conducting blocking material, like building structures or wooded areas, when there is no access to the space being measured for placement of sensors.

None of these systems account for the complexities in electrostatic field measurements caused by the presence of buildings and building materials with unknown building components. For example, no current EFT systems account for the impact on electrostatic fields of walls and metal conduits for electrical, water, and air ducts or the varying effects of wood, concrete and other construction materials that have unknown or only partially known distributions in a region of interest. Most ignore the environment and rely on temporal changes to distinguish differences from a fixed background state. Such systems would not work for detecting sleeping or stationary humans, for example.

These EFT systems also involve fixed and static geometries for sensors that make it difficult to adapt them to buildings of arbitrary shape and size and rapidly changing tactical situations. For example, U.S. published application No. US2002/0038096 by Gregory and Gregory published Mar. 28, 2002 (Gregory), which is incorporated by reference herein in its entirety, uses an array of sensors on a sensor holder that fixes the geometry of the sensors and therefore fixes the region to be measured. The use of fixed spacing between electrodes allows certain quantities in the inversion process to be pre-computed. Inversions using such pre-computed quantities cannot be performed for electrode spacing that is changing on tactical scales.

No systems exploit the properties of electrostatic fields to detect, locate and characterize one or more dielectric or conducting target objects, including biological entities, inside of at least partially unknown and variable building-sized regions.

Therefore, what is needed is a sensor technology that allows dielectric and conducting targets inside of building sized regions to be detected and characterized from the outside.

SUMMARY OF THE INVENTION

Techniques are provided for electrostatic imaging of a region to detect target objects completely inside the region. Embodiments based on these techniques allow biological entities, such as animals and humans, inside buildings or underneath wooden rubble or within wooded areas to be detected from outside the building or rubble or wooded area. This capability is useful in search and rescue. In some embodiments, these techniques also allow the orientation and armament of humans to be determined, as are useful in tactical situations involving military and police forces. In some embodiments, the dielectric properties of the one or more target objects within the search region may be probed over multiple frequencies, yielding information about the make-up of the target objects. In some embodiments, an autonomously reconfigurable network of independently moveable sensor nodes adapts to changing tactical conditions. The techniques include a system, a method, and a computer-readable medium.

According to one set of embodiments of the invention, an electrostatic imaging system includes multiple electrodes which, when positioned, instantaneously form a boundary of a search region. As used here, a "region" is a portion of space, such as a volume or a surface or a two-dimensional slice through a volume. Multiple emitter circuits connected to corresponding emitter electrodes are each configured for using its emitter electrode to produce an alternating current (AC) electric field with wavelength longer than about one hundred meters. Such long wavelengths are substantially in excess of the largest dimension of any object in the search region and are termed herein electrostatic fields. Multiple receiver circuits connected to corresponding receiver electrodes are each configured for using its receiver electrode to measure a property of an electric field produced, at least in part, by an emitter electrode. A processor determines a subset of less than all the plurality of emitter circuits to activate in sequence for determining a property of a dielectric target that is completely inside the search region.

According to one set of embodiments of the invention, a system for imaging a region to detect a dielectric target includes placing multiple electrodes along an outside perimeter of a search region (the instantaneous position of the constellation of the sensing electrodes define the search region). At least two electrodes are mounted to be moveable independently of each other. Emitter circuits are connected to corresponding emitter electrodes. Each emitter circuit is configured for using its corresponding emitter electrode to produce an electric field with wavelength longer than about one hundred meters. Receiver circuits are connected to corresponding receiver electrodes. Each receiver circuit is configured for using its receiver electrode to measure a property of an electric field produced, at least in part, by an emitter electrode. A processor determines a property of a dielectric target that is completely inside the search region based, at least in part, on measurements from the receiver circuits.

According to some embodiments of this set, none of the electrodes is positioned below the search region. In other embodiments nothing limits the distribution of the sensing electrodes or the orientation of the search region relative to the physical ground level. According to some embodiments of this set, the dielectric target is separated from the electrodes by a blocking material with a dielectric constant less than about 10. According to some of these embodiments, the blocking material is visually opaque, or one or more electrically conducting structures are embedded in the blocking material, or both. In some of these embodiments, the blocking material is not in contact with any electrode.

According to some embodiments of this set, an electrode is moved to enhance determining the property of the dielectric target by the processor. For example, one or more electrodes are moved to enhance surveillance of a wide search region. In another example, one or more electrodes are moved to more accurately determine the position or orientation of a particular target or to resolve multiple targets in relatively close proximity.

According to some embodiments of this set, an emitter circuit is configured to emit an electric field at multiple frequencies, and the processor determines a spectral response for the dielectric target. In some embodiments, the processor determines or controls the frequencies, or both. According to some of these embodiments, the processor distinguishes a biological target from a non-biological target based at least in part on the frequency dependent dielectric response for the dielectric target.

According to some embodiments of this set, while determining the property of the dielectric target, the processor determines to exclude a measurement from a particular receiver circuit. According to some of these embodiments, the measurement is excluded to improve the performance of determining the property of the target. For example, the processor enables one polling protocol that omits measurements from most receivers to more quickly determine the presence and approximate location of a target, and then, to more precisely fix the target, enables a different protocol that eliminates measurements not in the vicinity of the approximate location.

According to some embodiments of this set, the emitter circuits are operated sequentially in time in a particular order to improve determining the property of the dielectric target by the processor.

According to some embodiments of this set, an electrode is connected to both an emitter circuit and a receiver circuit.

According to some embodiments of this set, the receiver circuit is configured to measure an electrical potential of the electric field at a corresponding receiving electrode. According to some embodiments of this set, the receiver circuit is configured to measure a current induced by the electric field at a corresponding receiving electrode.

According to some embodiments of this set, the processor includes a forward computation that represents the dielectric target as an object that allows an analytical solution for the property of the electric field at the receiver electrode.

According to some embodiments of this set, an emitter circuit is configured to emit one or more temporal pulses of an electric field, each pulse including a combination of wavelengths longer than about one hundred meters.

In another set of embodiments of the invention, a system includes multiple electrodes, at least two of which are spaced apart more than about five meters. Multiple emitter circuits are connected to corresponding emitter electrodes. Each emitter circuit is configured for using a corresponding one of the emitter electrodes to produce an electric field with wavelengths longer than about one hundred meters. Multiple receiver circuits are connected to corresponding receiver electrodes. Each receiver circuit is configured for using a corresponding one of the receiver electrodes to detect an electric field produced, at least in part, by an emitter electrode. A processor determines a property of a dielectric target inside a region bounded by the electrodes based, at least in part, on measurements from the receiver circuits. The dielectric target has a dielectric constant greater than 10, and the dielectric target is separated from the electrodes by a blocking material with a dielectric constant less than 10.

In other sets of embodiments, a method and a computer-readable medium implement functions of the system.

As described in more detail below, electrostatic imaging is capable of penetrating buildings without damaging biological entities, and can readily distinguish biological entities, such as human beings, from other conductors and non-conductors found in buildings. Thus electrostatic imaging, using techniques described herein, can provide high-contrast, low-resolution images of the inside of a building from electrodes placed outside the building.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

A method and apparatus for building scale electrostatic tomography is described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Embodiments of the invention are described in the context of detecting the presence, location and possible armament of a human being inside a building in an urban setting. However, the invention is not limited to this context. In other embodiments, more or fewer properties of humans are determined, such as the orientation of the human (e.g., standing or reclining). In other embodiments, the properties of different biological entities, such as contraband animals, are determined. In some embodiments, the properties of the biological entities are determined in other settings, such as an expanse of trees, natural caves, or underground spaces, such as formed during landslides, avalanches, earthquakes, and other events involving search and rescue.

In the following a dielectric target, or simply "target," is a grounded or ungrounded object that has a finite dielectric response when probed at a given AC frequency. A small real number dielectric constant generally indicates a relatively non-conducting object. For example, a vacuum has a dielectric constant of one (1) and air has a similar value. A large dielectric constant generally indicates a conducting object. For example, some metals have dielectric constants over 109. Many commonly used building materials (i.e., dry wood, gypsum board, concrete or cement and the like) have a real component of dielectric constant of 10 or less. A biological entity generally has a real dielectric constant significantly greater than 10, and yet much less than a metal.

In the following description, the properties of low frequency electric fields are used to determine the properties of dielectric targets inside a search region, including, but not limited to, location, and the properties of one or more biological entities are inferred based on the measurements of properties of the electric fields. In other embodiments, the properties of low frequency magnetic fields, inherently associated with low frequency electric fields, are used to determine the magnetic permittivity of targets inside the search region, and the properties of one or more biological entities are inferred based on the measurements of properties of the magnetic fields.

Figure 1:
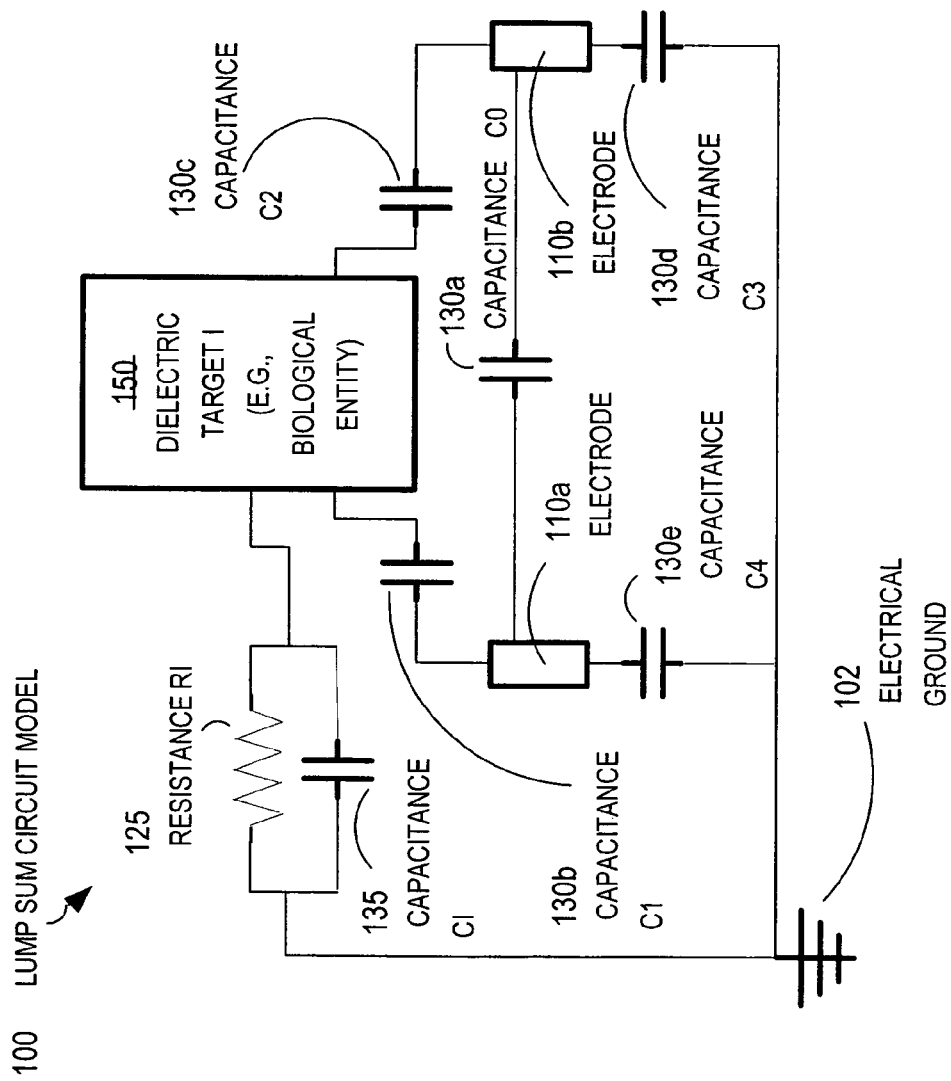
FIG. 1 is a block diagram that illustrates a lump sum circuit model, according to an embodiment.

The description is organized according to the following sections:
1. Functional Overview
2. Structural Overview
3. Example embodiments
3.1 A Two-dimensional Embodiment
3.2 A Three-dimensional Embodiment
3.3 Selective Placement
3.4 Selective Processing
3.5 Spectroscopic Detections
3.6 Processing for Noise
3.7 Hardware Components
4. Processor Hardware Overview 1. Functional Overview FIG. 1 is a block diagram that illustrates a lump sum circuit model of a human being and two electrodes, according to an embodiment. The human being is represented by dielectric target 150. The electrodes 110a, 110b are collectively referenced as electrodes 110. In one example, electrodes are objects in the control of a user, with high dielectric constants that are arbitrarily close to pure conductors.

A low frequency voltage signal is applied to an emitting electrode, e.g., electrode 110a. The low frequency electric field has long wavelengths compared to the size of the region being imaged. For example, to image inside a building larger than about 10 meters (m), electric fields with wavelengths longer than about 100 m are used. Such electric fields have frequencies lower than about 3 megaHertz (MHz, where 1 MHz=$10^6$ Hertz; and 1 Hertz, Hz=1 cycle per second).

In response to such a field, a displacement current flows from the emitter electrode to a grounded object, such as target 150, through the capacitive coupling between the emitter electrode 110a and the object. In the distribution of FIG. 1, displacement currents also flow through capacitive coupling between the emitter electrode 110a and the receiver electrode 110b and through the coupling between the target 150 and the receiver electrode 110b. The capacitive coupling is represented in FIG. 1 by capacitors 130a, 130b, 130c with capacitance values C0, C1, C2, respectively. The currents flow to ground potential 102 from the electrodes through capacitors 130d, 130e with capacitance values C3, C4, respectively. The displacement current internal to the target object flows to electrical ground potential 102 from the target object through internal capacitor 135 with capacitance CI and internal resistor 125 with resistance RI. The existence of RI indicates that the target 150 may have a direct path to ground potential 102 in addition to the capacitive coupling CI to the ground potential 102.

In some embodiments, the electric field is sensed by measuring the induced displacement current through the electrodes. The difference between the current flowing through the emitter electrode 110a and the displacement current flowing through the receiver electrode 110b is due to displacement currents induced in nearby dielectric objects, such as target 150. To infer the properties of the target from the difference in currents, the mechanism of the coupling is determined, based on the coupling of the target 150. In one example, three mechanisms are involved in inducing currents in the target 150 or receiver electrode 110b or both. These mechanisms are termed the loading mode, the emitter mode, and the shunt mode. These modes are described in more detail in *Gershenfeld I, II, III* and in J. R. Smith, IBM Systems Journal, Vol. 35, No. 384, 1996 (hereinafter Smith), which is incorporated by reference herein in its entirety.

In the loading mode, the current measurement is related to the capacitance between the emitter electrode and a dielectric object. No receiver electrode is involved. As the distance between them changes, the current through the emitter changes, e.g., the object's load on the emitter changes. For example, as the distance between the electrode and target 150 decreases, the loading mode induced current through the emitter increases. The loading mode is utilized in stud finders and security systems described above.

The emitter mode is related to the loading mode. The emitter mode occurs when the emitter is strongly coupled to a dielectric object. For example, the emitter mode becomes important at very short distances between target 150 and emitter electrode 110a, when the capacitance between the emitter and the target is large and the target is essentially at the same electrical potential as the emitter. The target essentially becomes an extension of the emitter. For example, in the emitter mode, the capacitance C1 of capacitor 130b is orders of magnitude greater than either C0 of capacitor 130a or C2 of capacitor 130c. The emitter mode is also important when the target body is in electrical contact with the emitter. As the distance between the target and the receiver decreases, the capacitance between them increases and the displacement currents at the emitter and the receiver increase. The change in emitter mode displacement current is proportional to the distance between the target and the receiver. For a target object close in potential to one of the electrodes 110a, 110b, the emitter mode displacement current depends on which of electrodes 110a and 110b is the emitter electrode and which is the receiver. The emitter mode is used in many proximity and intrusion detection systems.

The shunt mode dominates when the capacitance between the emitter electrode and target is about the same order of magnitude as the capacitance between the target and the receiver and the capacitance between the emitter and the receiver. For example, the shunt mode dominates when capacitance C0 of capacitor 130a is about the same order of magnitude as the capacitance C1 of capacitor 130b and capacitance C2 of capacitor 130c. Therefore, as a target approaches the emitter and receiver from a great distance, the capacitance to the emitter increases, inducing more current through the target, reducing the current through the receiver, and decreasing the capacitance between the emitter and receiver. This occurs because the field lines and associated displacement current that had been flowing to the receiver are now effectively shunted to ground through the target. Furthermore, as the target moves between the emitter and receiver, the capacitance C0 of capacitor 130a changes, because the dielectric constant of the target body replaces the material (e.g., air) with a different dielectric constant. Both effects occur simultaneously, and the relative importance depends to some extent on how well the target is grounded.

The shunt mode is favored for detecting the presence of a target, and for locating and tracking the target, and, with enough measurements, for estimating the size, shape or orientation of the target in the region. The shunt mode measurements are symmetric, so that a measurement of the displacement current in electrode 110b from emitter electrode 110a is the same as a measurement of the displacement current in electrode 110a from an emitter electrode 110b.

With shunt mode measurements using n electrodes, one can make n*(n−1)/2 measurements (which approaches $n^2/2$ for large values of n) by letting each electrode act as an emitter for one set of measurements. With loading mode measurements, n electrodes yield only n measurements. The extra measurements allow shunt mode measurements to distinguish conductor distributions that yield identical loading mode measurements, for example as described in Smith.

Based on $n^2/2$ measurements of displacement currents from n electrodes, a distribution of charges on the boundaries between different dielectric materials in a region (e.g., the distribution of charges on target object 150) is inferred using inverse methods in some embodiments. Any inverse methods that apply to electric fields may be used. For example, the inversion methods described in Fan or Gregory may be used. The relative performance of several inversion methods are described in more detail below.

In some embodiments, electrical potential of the electric field is measured instead of displacement currents. When the electric potential is used, the emitter electrode is charged to reach a particular electrical potential (e.g., 200 Volts, V) relative to ground and the potential relative to ground at the receiver electrode is measured. When displacement currents are used, currents are measured to maintain a particular charge (e.g., a particular number of Coulombs) on the respective electrodes. In one embodiment, electric potential is measured rather than electric current, because electric potential measurements are often less susceptible to noise then are electric current measurements.

The capacitance 130a between electrodes 110a and 110b depends on the dielectric constant of the target 150 as well as the dielectric constant of the intervening material, (such as air and building materials), and distance between the target 150 and the electrodes 110, and the grounding effects on various non-homogeneous elements. The dielectric constants are very different for different materials of interest, providing a high contrast signal. For example, the dielectric constant of air is 1, the dielectric constant of stone, brick and wallboard is about 3 at 3 MHz, the dielectric constant of human flesh is about 7000 at 3 MHz, and the dielectric constant of metal, such as in a rifle or other weapon, is about $10^6$ at 3 MHz.

Targets with dielectric constants on the order of human flesh could indicate the presence of humans in the region. Targets with constants on the order of metal in close proximity to the humans suggests the presence of armed humans. Non-target dielectric objects within the buildings, such as ductwork and wiring affect the measurements and inversions. Information about the existence and location of such building dielectrics, if known, can be used to simplify or improve the inversion computation.

In some inverse methods, called iterative methods, an initial distribution of dielectric bodies of interest (e.g., representing humans and personal armaments, walls, floors and ductwork, among others) is assumed. The electric field measurements at the electrodes are computed and compared to the actual measurements. Then the initial distribution is perturbed to generate computed values that agree more closely with the measurements. In some inverse methods, called non-iterative methods, linear systems of equations for the electric field based on the target properties of interest are solved.

In some embodiments, the electrodes are moved with respect to each other to obtain measurements that better resolve ambiguities in the properties of the inferred charge or dielectric distributions. For example, electrodes can be moved in the vicinity of a target to determine whether the target is composed of one or more than one dielectric objects separated by air. As described in more detail below, in some embodiments, the electrodes are moved to be about 50% above the dielectric objects, relative to an electrical ground plane.

When a solution is obtained for one region, the electrodes may be moved to make measurements in a different region intersecting the building of interest or any other new region of interest.

Figure 2:
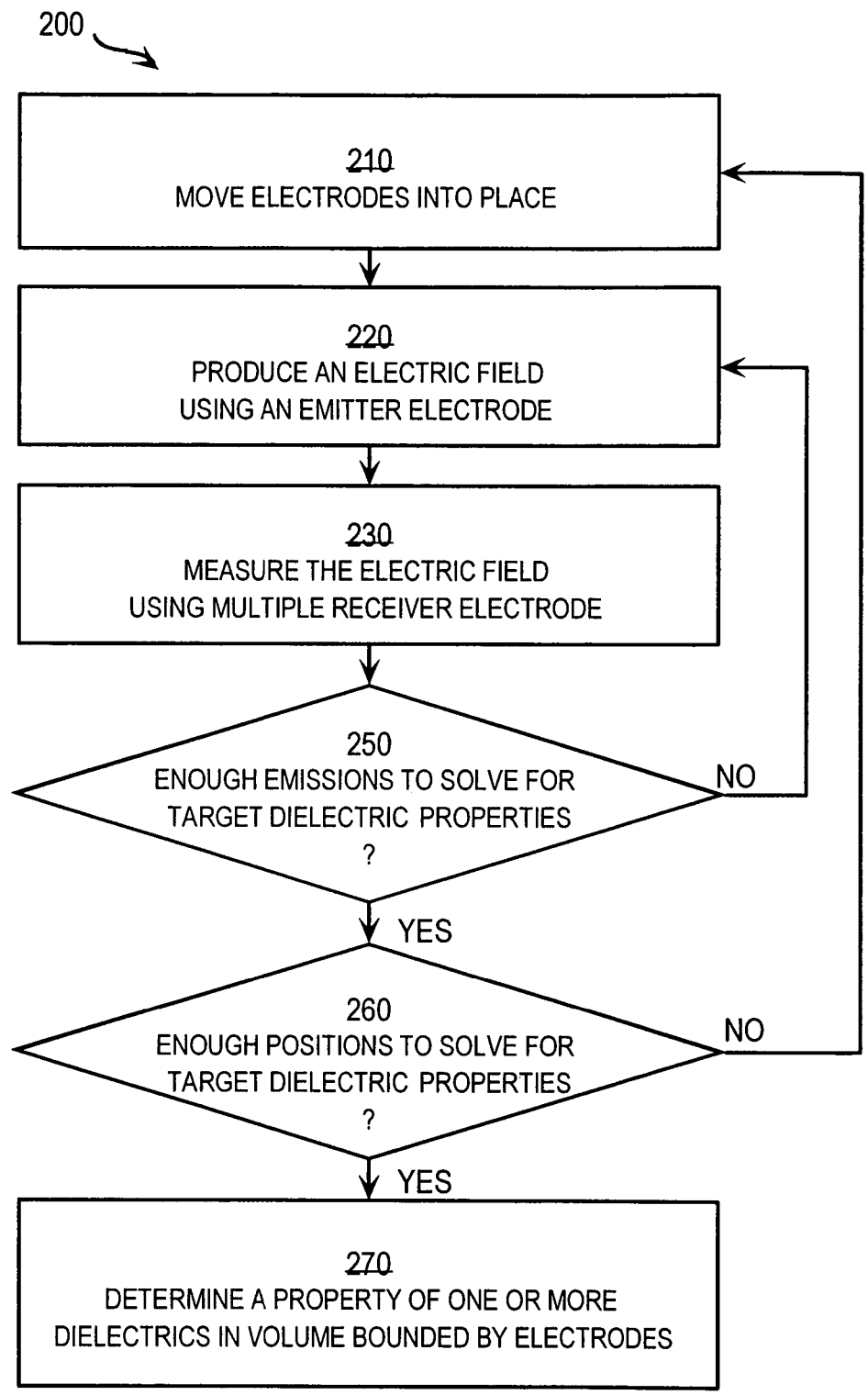
FIG. 2 is a flow chart that illustrates a method for imaging a region, according to an embodiment.

FIG. 2 is a flow chart that illustrates a method for imaging dielectrics inside a region, according to an embodiment. Although steps are shown in FIG. 2 in a particular order for purposes of illustrating an embodiment, in other embodiments some steps may be performed in a different order or overlapping in time.

In step 210, multiple electrodes are moved into place around a region of interest, such as a building or portion thereof, an extent of forest, or a pile of rubble. In some embodiments, multiple electrode assemblies that include the electrodes are passively moved into place by a moveable platform such as a troop, a robot, or an unmanned aerial vehicle (UAV). In other embodiments, the electrode assemblies include a movement mechanism, and a central unit sends commands to the electrode assemblies, thus causing them to activate the movement mechanisms to move to particular positions around the region of interest. When in place around the region of interest, in some embodiments, at least two electrodes are spaced apart more than about 5 meters. Step 210 includes shifting positions of one or more electrodes after those electrodes were initially placed around a region of interest. Step 210 includes shifting positions of most or all of the electrodes to image a second region of interest adjacent to, or overlapping with, or separated from, a first region of interest. In some embodiments, step 210 includes sending position data to the central unit indicating the position of each electrode.

For example, 200 electrodes are placed around a 10 m square building on 40 moveable platforms, one electrode assembly per platform, five electrodes per electrode assembly, ten moveable platforms per side of the building. Electrodes on diagonally opposite platforms are more than 10 m apart. Data indicating the approximate positions and orientations of the 40 electrode assemblies are sent to the central unit, from which the central unit can determine the position of each electrode on each electrode assembly.

In step 220, an electrostatic field is produced using at least one of the electrodes as an emitter. The electrostatic field has a wavelength long compared to the maximum distance between electrodes. In an illustrated embodiment, the frequency is 50 kHz and the wavelength of the electrostatic field produced is about six kilometers. The electrostatic field has a field strength to produce measurable signals at multiple electrodes acting as receivers, including a receiver over 10 meters from the emitter. In some embodiments, the electrostatic field includes multiple frequency components or is produced in multiple pulses at one or more frequencies. In some embodiments, step 220 includes receiving data from the central unit indicating the properties of the electrostatic field to emit. For example, one of the electrodes in one of the electrode assemblies emits a 200V, 50 kHz pulse for 2 milliseconds.

In step 230, the electric field is measured at multiple electrodes acting as receivers. The receivers may make the measurement using any method known in the art. For example, in some embodiments, each receiver makes a current measurement at a grounded electrode to determine the total capacitance between the current emitter and the receiver. In some embodiments, each receiver makes a measurement of electrical potential at its position relative to ground. In some embodiments, step 230 includes transmitting data indicating the measurement made and the position of the receiver to the central unit. In some embodiments, step 230 includes storing the measurements and processing the measurement data into position information for later transmission to the central unit. In some embodiments, step 230 includes receiving data from the central unit indicating whether the electrode assembly should make a measurement, or, if made, whether the electrode assembly should transmit the measurement to the central unit or store the measurement for later transmission.

In some embodiments a polling protocol is used to enhance surveillance of certain sub-regions of interest. For example, electrode assemblies that are relatively far away from a region of interest can be polled at a relatively lower rate than electrode assemblies that are proximate to the sub-region of interest, or are in more favorable geometries, or otherwise positioned to obtain higher signal-to-noise ratio signals. Polling strategies also enable a greater percentage of available communication and computational resources to be dedicated to surveillance of detected targets in the sub-region of interest, while not compromising a wide area surveillance function. The polling protocol determines which measurements are made during step 230. The polling protocol to implement during step 230 is determined by the central unit and communicated to the electrode assemblies, in some embodiments. In some embodiments, processors on one or more electrode assemblies participate in the determination of which polling protocol to implement.

For example, measurements of current are made at 150 electrodes on 30 electrode assemblies on 30 platforms spread over three sides of the building different from the emitter side of the building. Measurements by electrodes on the same building side as the emitter are avoided or ignored as providing too little information at too great a cost in data processing capacity, as described in more detail in a later section.

In step 250, it is determined whether enough emissions have been made to solve for the desired properties of a dielectric target. In some embodiments, step 250 includes determining that the same electrode should emit another electrostatic field at another frequency to determine the frequency response of one or more dielectric targets. In some embodiments, step 250 includes performing one or more inversion methods to obtain intermediate solutions that are used to determine whether another emission from another electrode is desirable. In some embodiments, step 250 includes determining whether a particular polling protocol has been completely executed.

For example, the central unit determines that an image of dielectric constants is to be reproduced on a grid that is 50×50 in a horizontal section of the search region using a non-iterative inversion method. In such an embodiment there are 2500 unknowns. Because each emitter yields 150 measurements, at least 17 independent sets of measurements are needed for this embodiment. With more measurements, error minimization, such as least squares, can be employed. In step 250, it is determined that an electrostatic field should be emitted from another electrode until emissions from at least 17 different electrodes are obtained. For example, the central unit determines that electrostatic fields should be emitted only from every fourth electrode (50 electrodes) to save time and power by collecting only data that are not redundant. In some embodiments other patterns of emitting electrostatic fields are used. For example, the next electrode to emit is 30 electrodes from the last electrode to obtain the first few measurements from the most widely spaced emitters to more quickly develop approximate solutions. If, based on the approximate solutions, the central unit determines that there is a cluster of grid locations with human dielectric constants in one corner of the current region, then the processor determines that closely spaced or adjacent emitter electrodes should be activated in sequence to distinguish whether these are multiple objects, such a two petite people, or a single object, such as a reclining or large person.

If it is determined in step 250 to emit another electrostatic field, then control passes back to step 220 to produce an electrostatic field using an emitter electrode. If it is determined in step 250 that no further electrodes should emit an electrostatic field using the current placement of electrodes, then control passes to step 260.

In step 260, it is determined whether measurements have been obtained at enough positions to solve for the desired properties of a target dielectric. In some embodiments, step 260 includes performing one or more inversion methods to obtain intermediate solutions that are used to determine whether movement of one or more electrodes is desirable For example, based on initial solutions or approximations, the central unit determines that electrodes should be more closely spaced in one corner of the building. In another example, the central unit determines that the electrodes should shift positions a small random amount to obtain more independent measurements of the same region. In another example, the central unit determines that the electrodes should move to make measurements in another overlapping, or adjacent, or separate region. For example, the central unit determines that there is a cluster of grid locations with human dielectric constants in one corner of the current region, and several electrode assemblies should move to that corner to help determine if one human is lying down or several humans are standing close to each other.

If it is determined in step 260 to move one or more electrodes, then control passes back to step 210 to move one or more electrodes into place. If it is determined in step 260 that no further electrodes should be moved to obtain this or another solution, then control passes to step 270.

In step 270, one or more properties of targets in the region are determined. For example, inverse methods are used to determine the number and location of objects that indicate humans inside a walled space based on measurements of the electric field obtained at the receiver electrodes. Any methods known in the art may be used or combined in step 270. Any information reasonably known or guessed can be included in the inversion process. In some embodiments, the orientation, movement, armament or other properties of the candidate human are also determined or estimated.

2. Structural Overview

Figure 3A:
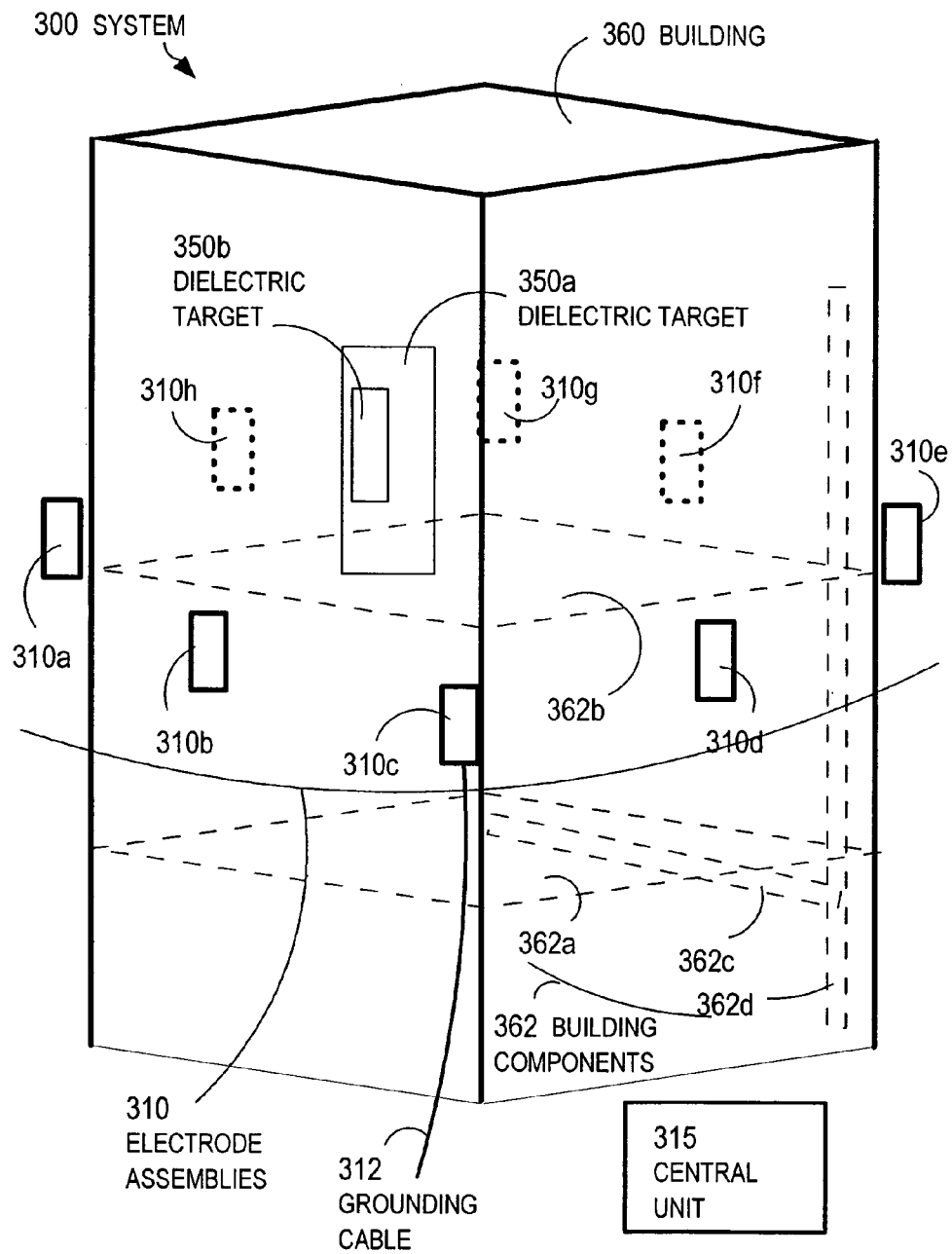
FIG. 3A is a block diagram that illustrates a system deployed outside a building to detect dielectric targets in images of the space inside the building, according to an embodiment.

FIG. 3A is a block diagram that illustrates a system 300 deployed outside a building 360 to image dielectric targets 350a, 350b inside the building, from the perspective of an observer standing outside one corner of the building, according to an embodiment. The dielectric targets 350a, 350b are collectively referenced herein as dielectric targets 350. In other embodiments more or fewer dielectric targets are inside one or more buildings or building rubble or other material with low dielectric constant compared to humans, such as an expanse of trees. In the illustrated embodiment, the dielectric targets 350a, 350b are not visible to the observer outside the building 360.

In addition to the dielectric targets 350, the building 360 also includes other dielectric objects. For example, the building 360 includes built-in fixed building components 362, such as walls, floors 362a, 362b, ductwork 362c, 362d, wiring and other fixed components. Some of these dielectric objects qualify as conductors with large dielectric constants and some qualify as insulators (e.g., non-conducting materials) with dielectric constants close to 1. Filing the gaps between these dielectric objects is air with a dielectric constant of about 1. The building components 362 are depicted with broken lines to indicate that they are not visible to the electrostatic sensor equipped observer ("observer") outside the building 360.

According to the illustrated embodiment, the system 300 includes multiple electrode assemblies 310, such as electrode assemblies 310*a*, 310*b*, 310*c*, 310*d*, 310*e*, 310*f*, 310*g*, 310*h*. The electrode assemblies behind the building 360 are drawn with broken lines to indicate they are not visible to the observer outside one corner of the building. In other embodiments more or fewer electrode assemblies are included. The electrode assemblies 310 include the emitter and receiver electrodes, and associated circuitry to generate electric fields and measure properties of the resulting electric fields. An embodiment of an electrode assembly 310 is described in more detail below with reference to FIG. 3C. In the illustrated embodiment, electrode assembly 310*c* includes a grounding cable 312 to maintain an electrical reference, e.g. local ground. One or more tethers 312 to ground may be required to provide an electrical reference to the electrode assemblies 310. Alternatively in certain over-specified cases, where there is an abundance of data measurements, the absolute reference of electrical ground might be inferred or calculated as part of the solution.

The system 300 also includes a central unit 315 for displaying the image of a region inside the building inferred by the system, including one or more properties of dielectric targets. An embodiment of central unit 315 is described in more detail below with reference to FIG. 3D. In other embodiments, additional central units are included or a central unit is included in one or more electrode assemblies, or both. In some embodiments additional processing is done by one or more additional processors, not shown. In some embodiments one or more central units or additional processors are remote from the site of building 360.

In the illustrated embodiment, the electrode assemblies 310 include movement mechanisms to position the electrode assemblies to make the measurements of interest. The electrodes and associated circuitry are mounted to the movement mechanisms so that the emitters and receivers can be moved to the measurement positions of interest to image a region of interest. In other embodiments, the electrode assemblies are mounted to external movement mechanisms, such as troops who carry the electrode assemblies to the measurement positions of interest when the electrostatic fields are safe, e.g., are less that the occupational and/or governmental health and safety standards for exposure to electrostatic fields. For example, in various embodiments, the electrode assemblies are mounted on, or include, robotic platforms that can scale the walls of buildings, or are mounted on, or include, UAVs, or some combination of these. An example UAV is the 34-inch diameter iSTAR Scaleable vertical takeoff and landing (VTOL) UAV system with a payload capacity of 30 pounds and a mission endurance of about two hours developed by DARPA.

Figure 3B:
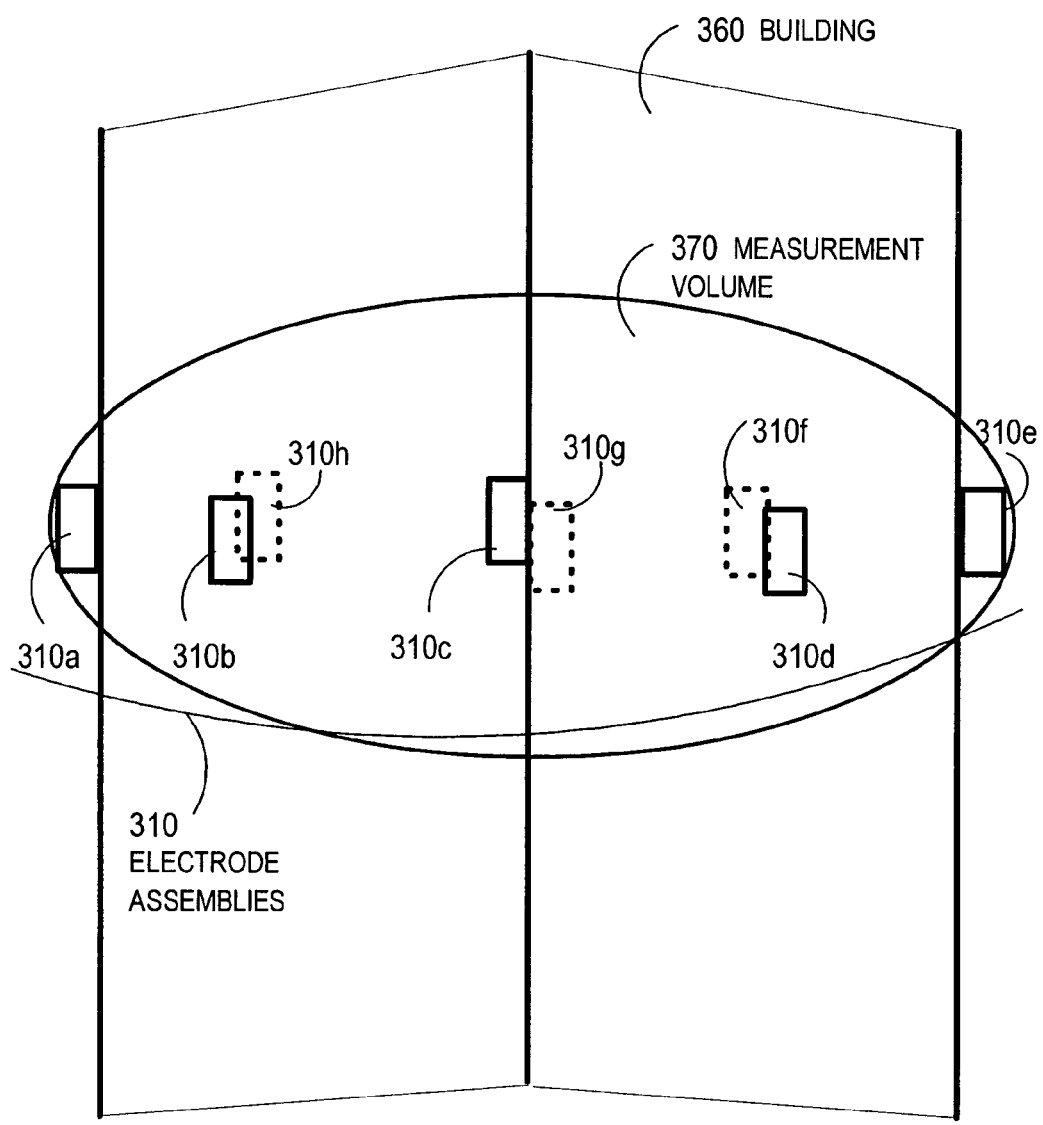
FIG. 3B is a block diagram that illustrates a region imaged by the electrode assemblies of FIG. 3A, according to an embodiment.

FIG. 3B is a block diagram that illustrates a region 370 imaged by the electrode assemblies of FIG. 3A, according to an embodiment. The region is shown in a lateral view relative to a plane that deviates from the center of each electrode in each electrode assembly 310 by a minimum amount. The region qualitatively represents electric field lines whose intersection with a target appreciably impacts the shunt mode. Other regions in which these electrodes may detect dielectrics, such as regions above or below the primary region of interest, are not shown. According to Smith, the region affected by the shunt mode may extend twice the dipole distance between the emitter and receiver in a direction perpendicular to the line segment connecting emitter and receiver. The purpose of showing region 370 is to indicate that not all of the building 360 need be imaged by one arrangement of electrodes. Instead, the electrodes can move over the outside surface of the building 360 to successively image different regions inside the building 360. There may be operational situations where it is not possible or practical to deploy or position electrode assemblies over all 4 exterior surfaces of the surveillance region. The invention is capable of converging to solutions of target position and other properties if less than 360 degree coverage is available, but with a compromise in location estimate accuracy. Because of the special geometry of a building, such as building 360, it is impractical to position an electrode assembly beneath the building. Therefore no electrode assembly is positioned beneath the region 370 in the illustrated embodiment.

As the dipole distance increases, either the receiver sensitivity, emitter voltage or both may need to be increased, to be detected at the receiver electrode. It is anticipated that the emitter voltage can not be increased indefinitely, because at some breakdown voltage, electrical current may arc directly to ground or to the building structure itself or produce fields that exceed health and safety standards. As indicated in the simulations below, a voltage of about 200 Volts is sufficient to generate signals that are detectably affected by dielectric targets inside modest size buildings, such as building 360.

2.1 Electrode Assembly.

Figure 3C:
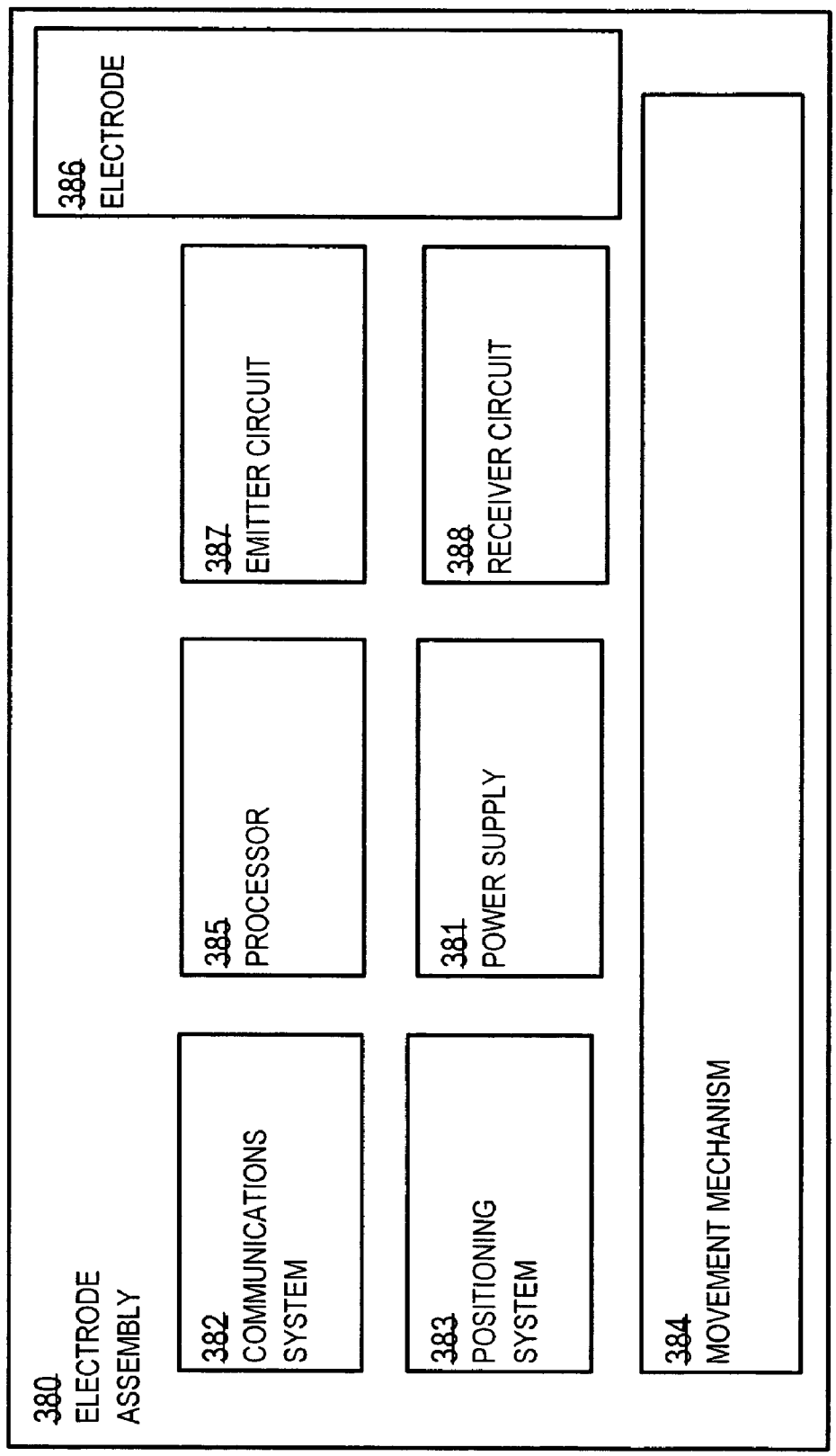
FIG. 3C is a block diagram that illustrates an electrode assembly, according to an embodiment.

FIG. 3C is a block diagram that illustrates an electrode assembly, according to an embodiment 380. The electrode assembly 380 includes a power supply 381, an electrode 386, an emitter circuit 387 and a receiver circuit 388. In addition, the electrode assembly 380 includes a communication system 382, a positioning system 383, a processor 385, and a movement mechanism 384.

The power supply 381 provides power for the emitter circuit 367, receiver circuit 388, processor 385, communication system 382 and positioning system 383. Any power supply known in the art may be used, including any electrical power supply. Although shown as a separate component in FIG. 3C, in other embodiments the power supply 381 is part of one or more of the other components. In the illustrated embodiment, the movement mechanism 384 includes a separate power supply for a different kind of power. In other embodiments, the movement mechanism is powered by power supply 381.

In the illustrate embodiment, the electrode 386 is a conductor that is used both as an emitter electrode and a receiving electrode. In other embodiments, separate conductors are used as emitter electrodes and receiver electrodes. In some embodiments each electrode assembly includes multiple electrodes spaced apart from each other, each of which may be operated as an emitter or a receiver using one or more emitter circuits 387 and receiver circuits 388. For example, in some embodiments each electrode assembly includes five electrodes spaced apart by 0.2 m to form an array 0.8 m long. In some embodiments, an electrode assembly includes either an emitter circuit 387 or a receiver circuit 388, but not both. In some embodiments, an electrode assembly includes a different number of emitter and receiver circuits or electrodes or both.

The emitter circuit 387 is an electric circuit that generates a voltage on electrode 386 relative to a reference electrical potential as needed to perform electrostatic tomography. For example, the emitter circuit 387 generates a prescribed low frequency electric voltage on the electrode 387 relative to a reference potential and determines the current consumed to generate that voltage. The consumed current is related to the loading mode capacitance. In some embodiments, the emitter circuit includes a physical mechanism to maintain the reference potential, such as a grounding cable 312, or a connection to a grounding cable in the receiver circuit, described below. In some embodiments that do not use information in the loading mode capacitance, the emitter circuit does not determine the current consumed to generate the prescribed low frequency voltage.

In some embodiments, the emitter circuit generates a train of one or more pulses, each pulse composed of one or more low frequency AC electric fields. In such embodiments the duration of each pulse is long compared to the period of the electric field being used. For example, if the electric fields used are 100 kHz to 3 MHz, (periods of $10^{-5}$ seconds, s, to $3 \times 10^{-7}$ s), then the pulse length is long compared to $10^{-5}$ s. Such a sequence of pulses can be used to distinguish signals generated from these particular electrodes from signals generated by other active or emitting electrodes or by noise or by jamming systems.

The receiver circuit 388 is an electric circuit that determines a property of the electric field at the electrode 386 caused by an electric field emitted by a different emitter electrode, usually on a different electrode assembly. In some embodiments, the receiver circuit 388 determines the electric field strength by measuring a current induced through the electrode 386 while the electrode is kept at the reference electrical potential, e.g., electrical ground. The measured current is related to the capacitance between the receiver electrode 386 and the emitter electrode caused by the shunt mode or the emitter mode or both. In some embodiments, the receiver circuit 388 determines the electric field strength by measuring the electrical potential at the electrode 386 relative to electrical ground while the electrode is kept insulated from electrical ground. The receiver circuit includes a mechanism to maintain the reference potential, such as a grounding cable 312, or a connection to grounding cable in the emitter circuit 387.

The capacitance and displacement currents for electric field sensing in these scenarios are sometimes small, on the order of picafarads ($10^{-12}$ Farads) and nanoamps ($10^{-9}$ Amperes), and microvolts ($10^{-6}$ Volts) as described in more detail below with respect to demonstrations of various embodiments. Therefore relatively sophisticated detection strategies are employed in the receiver circuit 388. Any detection strategy capable of making such fine measurements may be employed. For example, a synchronous detection circuit uses the frequency and phase of the remote emitter circuit as a very narrow band-pass filter to reject electrical signals not associated with the emitter, as contemplated by Gershenfeld and Smith. The emitter frequency and phase can be determined using the communication system 382 described below. In other embodiments, detection strategies include, but are not limited to, frequency-modulation chirps, frequency hopping, and code modulation, such as a spread spectrum, as used in RADAR.

The communication system 382 is a component that sends information to the central unit 315. Any method known in the art may be used for the communication system, including tethered and wireless communications systems using radio, optical or other transmission signals. For example, the communication system 382 sends to the central unit 315 data indicating the electrical potential measured by the receiver circuit 388. In the illustrated embodiment, the communications system 382 also receives information from the central unit and other electrode assemblies. For example, the communication system 382 receives data from the central unit 315 that indicates instructions from the central unit 315, such as when and what signal to emit and where to move. As further examples, the communication system 382 receives data from one or more other electrode assemblies, such as data indicating the phase and frequency emitted at the electrodes on those assemblies for a synchronous detection circuit.

The positioning system 383 is used to determine the approximate position of the electrode assembly 380, and hence the position of the electrode 386, relative to other electrodes and to the building. Any system known in the art for determining the position of the electrode assembly may be used. For example, a global positioning system (GPS) can be used to determine the ranges between electrode assemblies and to determine the position of one or more electrode assemblies relative to one or more reference stations that are fixed for the duration of the imaging procedure.

The processor 385 is an information processor, such as a computer board or microprocessor, which obtains data from one or more of the other components or sends control data to one or more of the other components, or performs some combination of these functions. In some embodiments, the processor 385 includes one or more data storage devices, as described in a later section. In the illustrated embodiment, the processor 385 controls the timing and signal characteristics of the emitter circuit based on data received from the central unit 315 through the communications system 382. The processor 385 also controls the characteristic settings of the receiver circuit based on data received from the central unit 315 through the communications system 382. and receives data indicating the measured displacement current or electric potential from the receiver circuit 388 or emitter circuit 387 or both and sends data based on such measurements to the central unit 315 through communications system 382. The processor also manages the other components, for example, by sending configuration information to those components or monitoring diagnostic signals from those components. In some embodiments, the processor 385 also controls the movement mechanism 384 to position the electrode assembly 380 in response to the measurements received from the receiver circuit 388 or data received through communications system 382 or based on internal rules-based decisions.

The processor 385 may also do some computations for the inversion problem based on the measured data or data received through communications system 382 or both. By performing computations on processor 385, at least some of the computational load of the inversion problem is distributed among one or more electrode assemblies with or without the central unit 315. In the illustrated embodiment, the processor 385 and communication system 382 on multiple electrode assemblies, with or without a central unit 315, form a communication network. Any network communication protocol known in the art with appropriate characteristics may be used.

The movement mechanism 384 causes the electrode assembly 380 to change its position relative to a building or relative to one or more other electrode assemblies, or both. For example, electrode assembly 380 may be commanded to move by central processor unit 395 to configure the network with a more favorable geometry to resolve ambiguities in reconstructed dielectric target position or to aggregate sensing resources in one particular area to enhance resolution. While any feedback mechanism known in the art and consistent with the physics of the exemplar could be employed, the covariance of the dielectric object position estimates could be used to generate filtered movement commands for one or more electrode assemblies to reposition to new positions to minimize the covariance of the reconstructed dielectric target object position estimates. Any movement mechanism known in the art may be used which positions the electrode assembly as desired for a particular application. In some embodiments, the electrode assembly includes a wall climbing robot or a UAV or some other moveable platform. In some embodiments, the movement mechanism 384 is omitted, and the electrode assembly 380 is mounted on a moveable platform, such as a human troop, a firefighter, a wall climbing robot, or a UAV, among other platforms, that is not directly controlled by the processor 385 or central unit 315. Alternatively, when the movement mechanism 384 is omitted the electrode assembly could be deployed in fixed locations, such as over a collapsed building or other rubble to image down through the rubble to identify buried and concealed humans. With electrodes fixed at a sufficient number of locations distributed around a search region, variable spatial sampling can achieved by polling that omits burdensome or redundant electrodes at each stage of processing.

2.2 Central Unit.

Figure 3D:
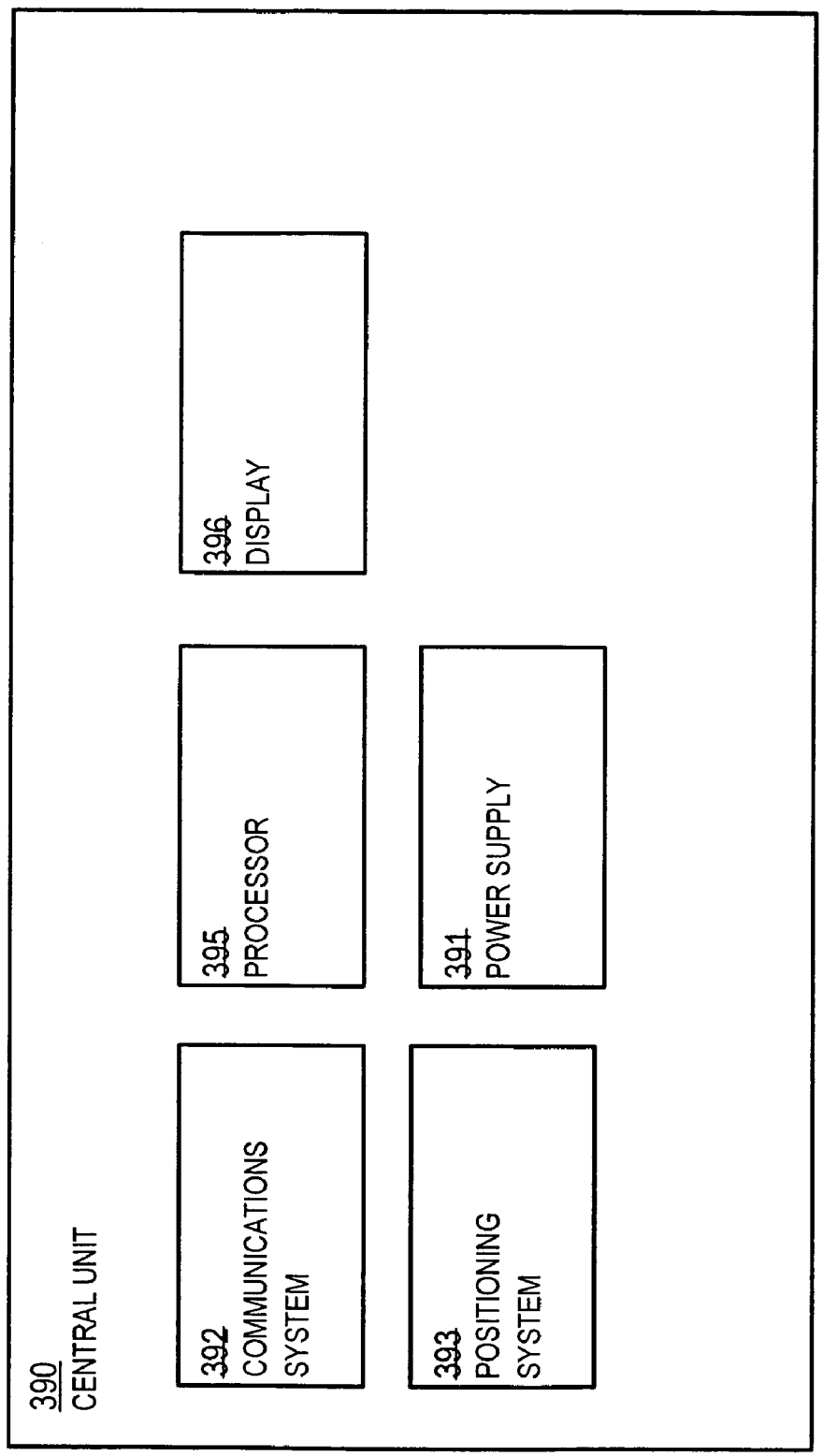
FIG. 3D is a block diagram that illustrates a central unit, according to an embodiment.

FIG. 3D is a block diagram that illustrates a central unit, according to an embodiment 390. The central unit 390 includes a power supply 391, a communication system 392, a positioning system 393, a processor 395, and a display 396.

The power supply 391 provides power for the other components. Any power supply known in the art may be used, including any electrical power supply. Although shown as a separate component in FIG. 3C, in other embodiments the power supply 391 is part of one or more of the other components.

The communication system 392 is a component that receives information from the electrode assemblies 310, such as electrode assembly 380. Any method known in the art may be used for the communication system, including tethered and wireless communications systems using radio, optical or other transmission signals. For example, the communication system 392 receives data indicating the electric potential measured by the receiver circuit 388 on electrode assembly 380, or computed values for the inversion problem. In the illustrated embodiment, the communications system 382 also sends information from the central unit. For example, the communication system 382 sends data to an electrode assembly 380 that indicates instructions, such as when and what signal to emit and where to move. In some embodiments, the communications system 392 uses one or more communication relay devices (not shown), external to the central unit 315, such as satellites and transceivers deployed between the central unit and one or more electrode assemblies.

The positioning system 393 is used to determine the position of the electrode assemblies, and hence the position of the electrodes thereon. Any system known in the art for determining the position of the electrode assemblies may be used. In some embodiments, the positioning system 393 is omitted from the central unit and is part of a separate system (not shown), such as a transponder reference system, for determining the positions of the electrode assemblies.

The processor 395 is an information processor, such as a computer board or microprocessor, which solves for a distribution of charges or properties of targets in one or more regions through the building, or both. In the illustrated embodiment, the processor 395 also obtains data from one or more of the other components or sends control data to one or more of the other components, or performs some combination of these functions. In some embodiments, the processor 395 includes one or more data storage devices, as described in a later section. In the illustrated embodiment, the processor 395 determines the timing and signal characteristics for the emitters on one or more electrode assemblies and the position of the electrode assemblies.

The display 396 is a device that presents the properties of one or more dielectric targets inside the search region for use by another system or human operator. For example, the display 396 is a computer monitor with symbols representing the building walls and the three dimensional position and orientation of human-type bodies within the building as well as the three dimensional position of rifle-sized and rocket-launcher-sized metallic objects for viewing by a troop commander.

3. Example Embodiments

Various simulations based on theory are performed that demonstrate the size of the signal that can be measured and the inversion approaches that can be used in various embodiments. The results of these simulations are described in the present section. The invention is not limited to these embodiments or by these simulations or by this theory.

The underlying field equation governing electrostatic tomography is the non-homogeneous Poisson equation, which can be derived from either of the following two Maxwell's equations given by Equations 1a and 1b $$\nabla \cdot D = \rho_f \quad (1a)$$

$$\nabla \times H = \partial D / \partial t + J_f \quad (1b)$$

combined with the constitutive relation, Ohm's Law, and the continuity equations given by Equations 2a, 2b, 2c, respectively $$D = \epsilon_0 \epsilon E \quad (2a)$$

$$J_f = \sigma E \quad (2b)$$

$$\partial \rho_f / \partial t + \nabla \cdot J_f = 0 \quad (2c)$$

where D, E, H are the electric induction, electric field, and magnetic field, respectively; $\rho_f$ and $J_f$ are the charge density and the electric current density, respectively; $\sigma$ and $\epsilon$ are the electric conductivity and the relative dielectric constant of the material; and $\epsilon_0$ is the electric field permittivity of the vacuum (=$8.85 \times 10^{-12}$ farads/m). For a system driven at frequency □ (in radians per second), either of Equations 1a, 1b reduces to the non-homogeneous Poisson's equation, given as Equation 3.

$$\nabla \cdot [\epsilon - j\sigma/\epsilon_0 \omega] E = 0 \quad (3)$$

where j is the square root of negative one (−1) and the terms in the square brackets [ ] can be considered a complex dielectric constant with a real part □ and an imaginary part $-\sigma/\epsilon_0 \omega$. The imaginary part has little effect on the measured signals when the real part is large, and so the imaginary part is not considered further in these simulations. Many materials, including human flesh, exhibit a change in the real part $\epsilon$ as a function of frequency ωas described in more detail in a later section. In the quasi-electrostatic approximation, the concept of electric potential is still valid and is defined as the scalar quantity Φ whose spatial gradient yields the vector electric field E, as given by Equation 4.

$$E = -\nabla \Phi \quad (4)$$

Simple substitution yields the homogeneous Poisson equation for the potential, given in Equation 5.

$$\nabla \cdot (\in \nabla \Phi) = 0 \quad (5)$$

The homogeneous equation applies when there are no net charges present in a region. In the presence of a charge q at a position x', the non-homogeneous Poisson's equation describes the electrical potential at position x, as given by Equation 6.

$$\nabla \cdot (\in \nabla \Phi) = -q\delta(x-x')/\in_0 \quad (6)$$

where δ represents the delta function that has a value of one (1) for an argument of zero and a value of zero (0) for other arguments. Equation 6 is the base equation that is used to formulate the inverse problem based on measured potentials.

The signals used to reconstruct the distribution of dielectric constants in the region originate from the response of dielectric constant inhomogeneities to a voltage source. The voltage source polarizes a dielectric object, and the polarized object generates additional potential on the outer boundary of the region to be imaged. The relevant and useful signal inverted in these simulations to reconstruct the distribution of dielectric constants in the region is the measured electric potential difference between the voltages on the outer boundary with and without the inhomogeneous dielectric objects in the region.

To maximize the useful signal, it is important that most of the electric field lines pass through the inhomogeneous dielectric objects, and should not short directly to ground. Placement of the source electrode relatively far from electrical ground can help maximize the useful signal.

3.1 A Two-dimensional Embodiment

Figure 4A:
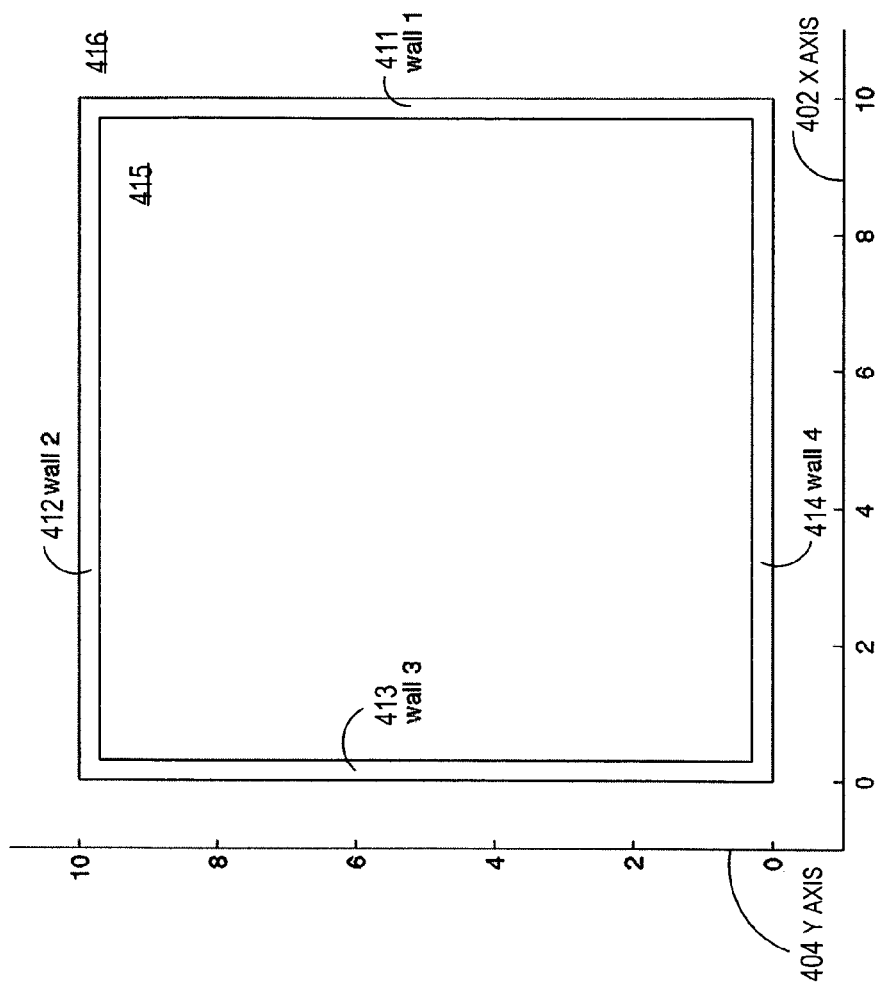
FIG. 4A is a block diagram that illustrates a region including four walls in a building-sized space, according to an embodiment.

A two-dimensional embodiment is described first because it is a relatively simple embodiment that demonstrates important concepts of use in many other embodiments. Consider the situation depicted in FIG. 4A. FIG. 4A is a block diagram that illustrates a horizontal cross section through a region including four walls in a building-sized space, according to an embodiment. The x axis 402 gives distance in meters in one horizontal direction; and the y axis 404 gives distance in meters in a perpendicular horizontal direction relative to an origin at an outside corner of two walls. Wall 411 represents a first wall of the building. Wall 412 represents a second wall of the building that is adjacent and perpendicular to the first wall 411. Wall 413 represents a third wall of the building that is adjacent and perpendicular to the second wall 412 and opposite to the first wall 411. Wall 414 represents a fourth wall of the building that is adjacent and perpendicular to the first wall 411 and opposite to the second wall 412. The walls are 0.3 m thick and have a dielectric constant of 4. The remaining area is filled with air having a dielectric constant of 1. The area 415 inside the four walls is to be imaged from electrodes placed in the area 416 outside the four walls.

3.1.1 Example Signal Strength in 2-D

Figure 4B:
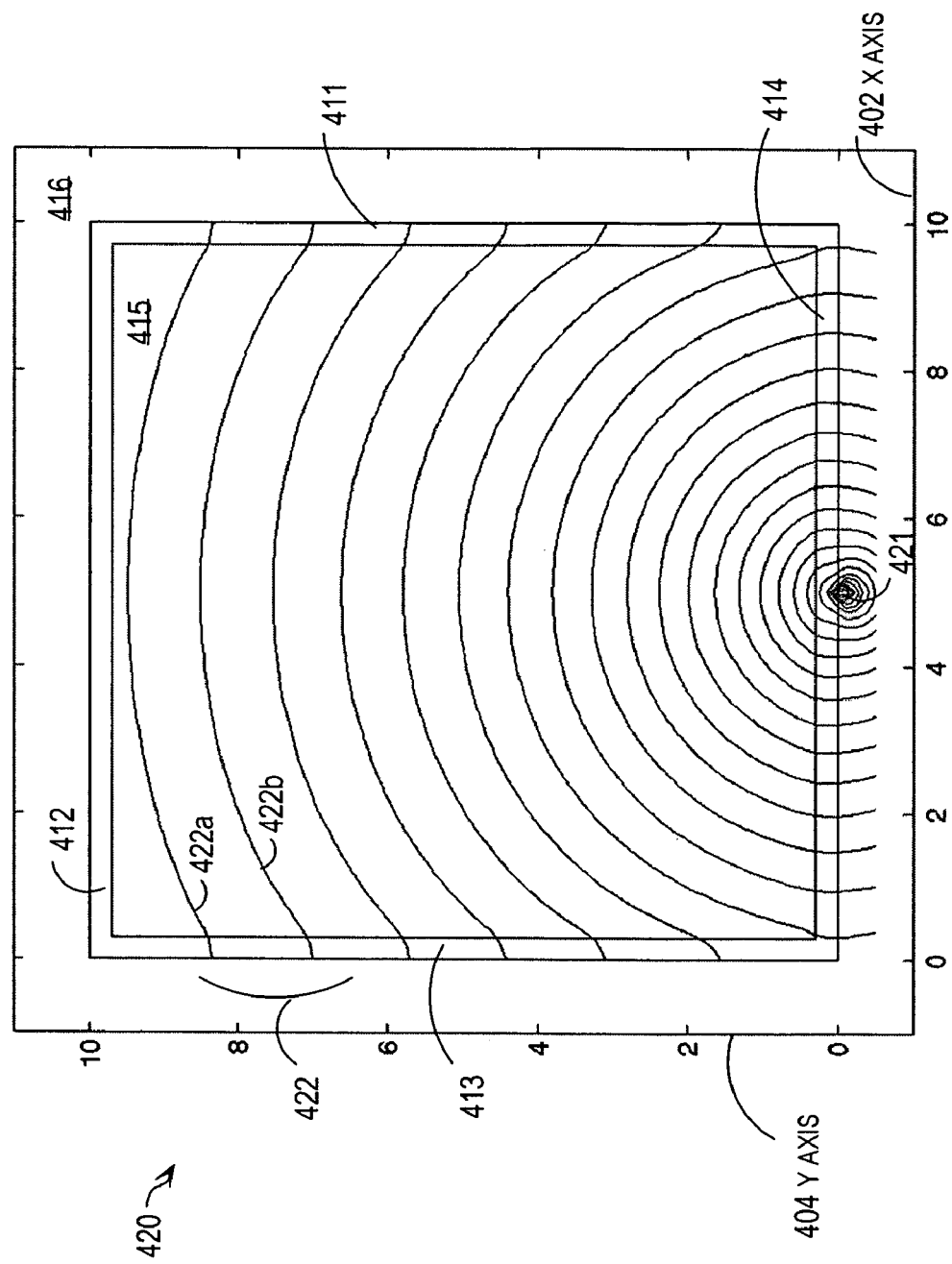
FIG. 4B is a graph that illustrates an electrical potential of an electric field in a horizontal slice through a region in a building-sized space, as generated by an electrostatic simulation model, according to an embodiment.

FIG. 4B is a graph 420 that illustrates an electric potential of an electric field in a horizontal slice through a search region in a building-sized space, as generated by an electrostatic simulation model, according to an embodiment. The electric potential is generated by solving the two-dimensional, non-homogeneous Poisson Equation (Equation 6) for multiple locations in the horizontal area. A numerical solution is obtained using the finite element method (FEM) well known in the art. This method solves a partial differential equation by dividing the complex geometry of the domain of interest into small elements (e.g., triangles in two dimensions) and linearizing the partial differential equation on each element. In the illustrated embodiment, a MATLAB™ Partial Differential Equation (PDE) tool based on the FEM is used to generate two-dimensional solutions for the electric potential in the area depicted in FIG. 4A encompassing zero or more two-dimensional cross sections of cylinders representing dielectric targets. MATLAB is a commercial software package available from MATLAB of Natick, Mass. The PDE tool was found to generate solutions that agree sufficiently closely with electric potential fields for which exact analytical solutions are known. The PDE solutions are thus used to generate the signal that is inverted to deduce the properties of the dielectric targets.

In FIG. 4B, x axis 402, y axis 404, and walls 411, 412, 413, 414 are the same as in FIG. 4A. A charged electrode is introduced as a source at source position 421, about 5 m along the outside of wall 414. To generate this two-dimensional rendering, there are no changes in the vertical dimension, i.e., the source is a vertical line source with a particular charge density per linear distance. The walls are extended vertically, as well. Contours 422 of equal electric potential are shown that decrease from a maximum at source position 421. The logarithm of the electric potential is plotted to show structure at low values. Adjacent contours differ by one milliVolt (mV, 1 mV=$10^{-3}$V) in electric potential. For example, contour 422a represents the locations of electric potential that is one mV less than the electric potential along contour 422b. Contours 422 include contours 422a, 422b among others that are not labeled. FIG. 4B shows the relatively mild effect of walls in perturbing the circular symmetry about the source position 421.

Figure 4C:
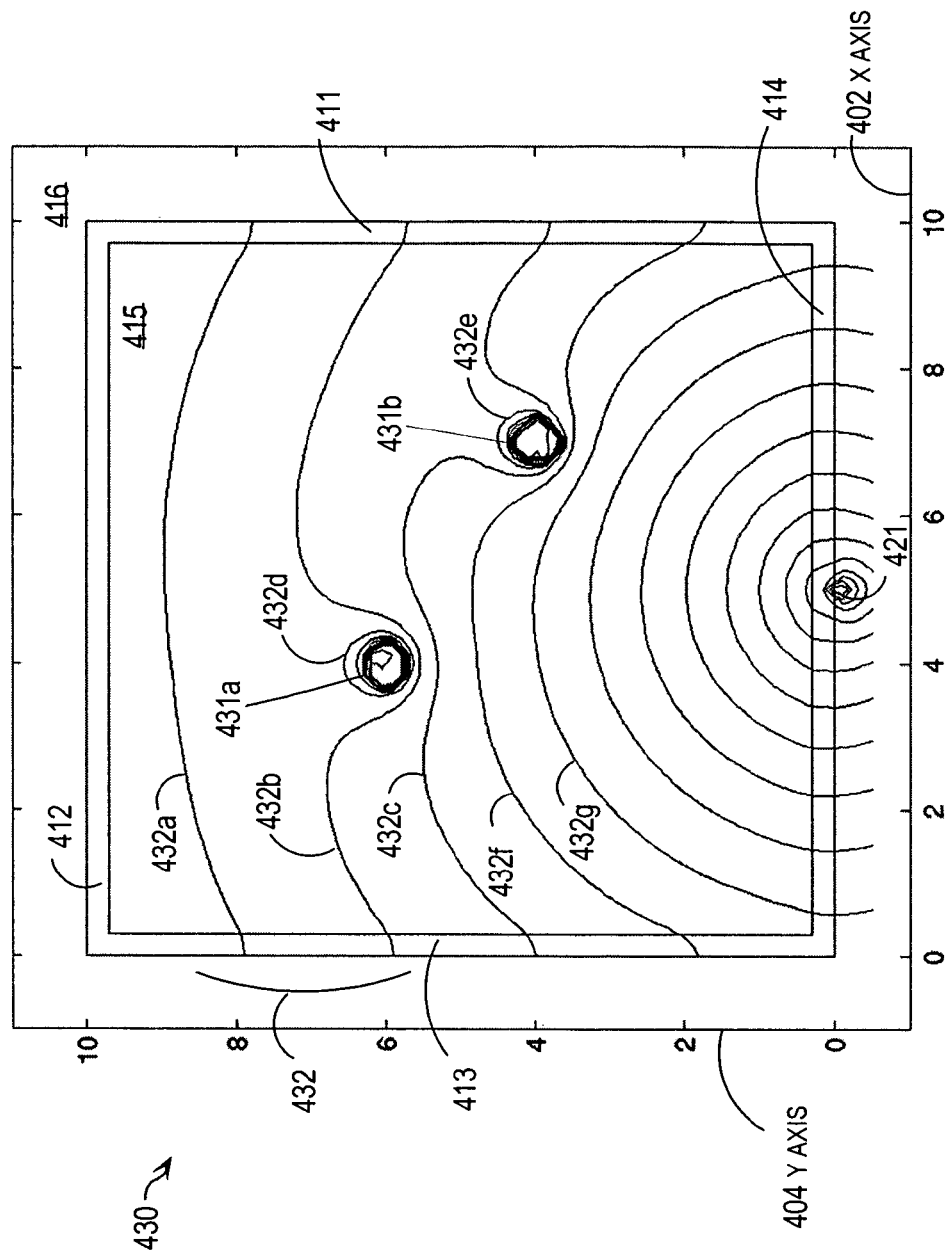
FIG. 4C is a graph that illustrates an electrical potential of an electric field in the horizontal slice of FIG. 3A when dielectric targets are present in the space, as generated by an electrostatic simulation model, according to an embodiment.

FIG. 4C is a graph 430 that illustrates an electric potential of an electric field in the horizontal slice of FIG. 4A when dielectric targets are present in the space, as generated by an electrostatic simulation model, according to an embodiment. In FIG. 4C, x axis 402, y axis 404, walls 411, 412, 413, 414 and source position 421 are the same as in FIG. 4B. Vertical cylinders 431a, 431b having dielectric constant of 80 and radius of 0.3 m are introduced at the locations shown by their circular cross sections at (x,y) coordinates of about (4, 6) and (7, 4), respectively. The range of data presented in FIG. 4C extends from a maximum of 200 Volts at the source position 421 to a minimum computed voltage potential of 26 milli-Volts. The contours 432 of electric potential are shown that decrease from a maximum at source position 421. The logarithm of the electric potential is plotted to show structure at low values. The data range of the logarithm of electric potential varies from −3.6 to 2.3 (log) Volts. Contours 432 include contours 432a, 432b, 432c, 432d, 432e, 432f, 432g, among others that are not labeled.

As clearly seen, dielectric targets 431a, 431b significantly perturb the electric potential in their vicinity, as shown by the contours 432b, 432c, 432d, 432e, 432f, which are unlike anything seen in FIG. 4B. However, measurements are not expected to be available in the areas where the contours are most perturbed, but rather along the outside of walls 411, 412, 413, 414 where the contours appear qualitatively similar to those in FIG. 4B. Though qualitatively similar, these simulations indicate that measurable differences occur outside the walls of the enclosed region. The differences are shown in FIG. 4D.

Figure 4D:
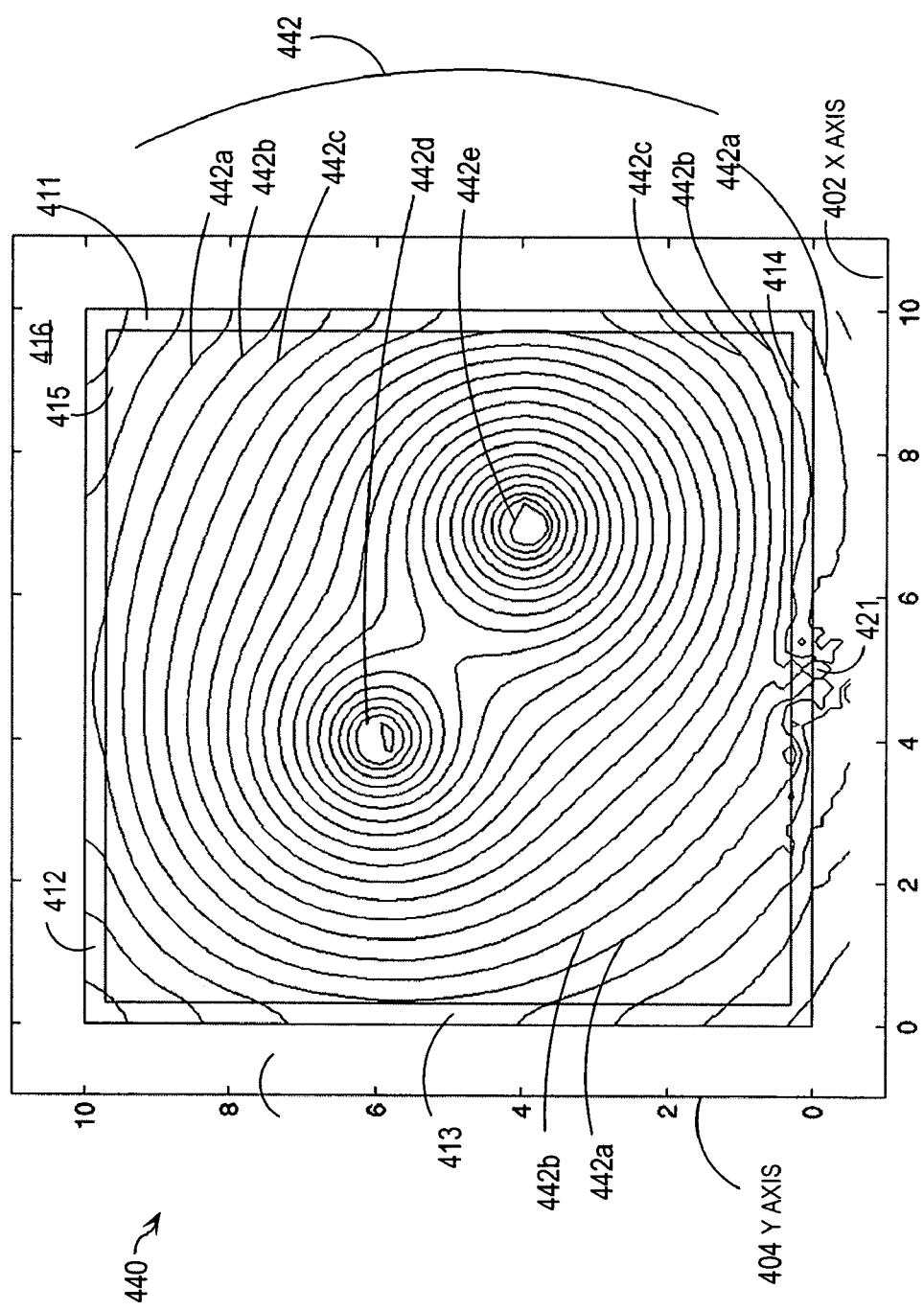
FIG. 4D is a graph that illustrates the difference in the electrical potentials of FIG. 4C and FIG. 4D, which is the signal due to the field induced in the space by the dielectric targets, according to an embodiment.

FIG. 4D is a graph 440 that illustrates the difference in the electric potentials of FIG. 4C and FIG. 4D, which is the signal due to the field induced in the space by the dielectric targets, according to the embodiment of FIG. 4C. To show spatial structure where the differences are small compared to the maximum difference, the arithmetic log of the difference is plotted. In FIG. 4D, x axis 402, y axis 404, walls 411, 412, 413, 414 and source position 421 are the same as in FIG. 4B. Contours 442 show electric potential difference between a range of −0.4 to 0 (log) Volts. Contours 442 include contours 442a, 442b, 442c, 442d, 442e, among others that are not labeled.

As clearly shown, relative maximum differences occur at the coordinate positions (4, 6) and (7, 4) of the cylinders 431a, 431b, as indicated by contours 442d, 442e. However, differences are also evident along the outside of the walls 411, 412, 413, 414. Also clear from contours 442a, 442b, 442c in FIG. 4D is that greater differences occur along wall 411 which is closest to either of the cylinders, than along walls 412, 413. Also evident in FIG. 4D is the convoluted character of the contours 442a, 442b, 442c in the vicinity of the source position 421.

Figure 4E:
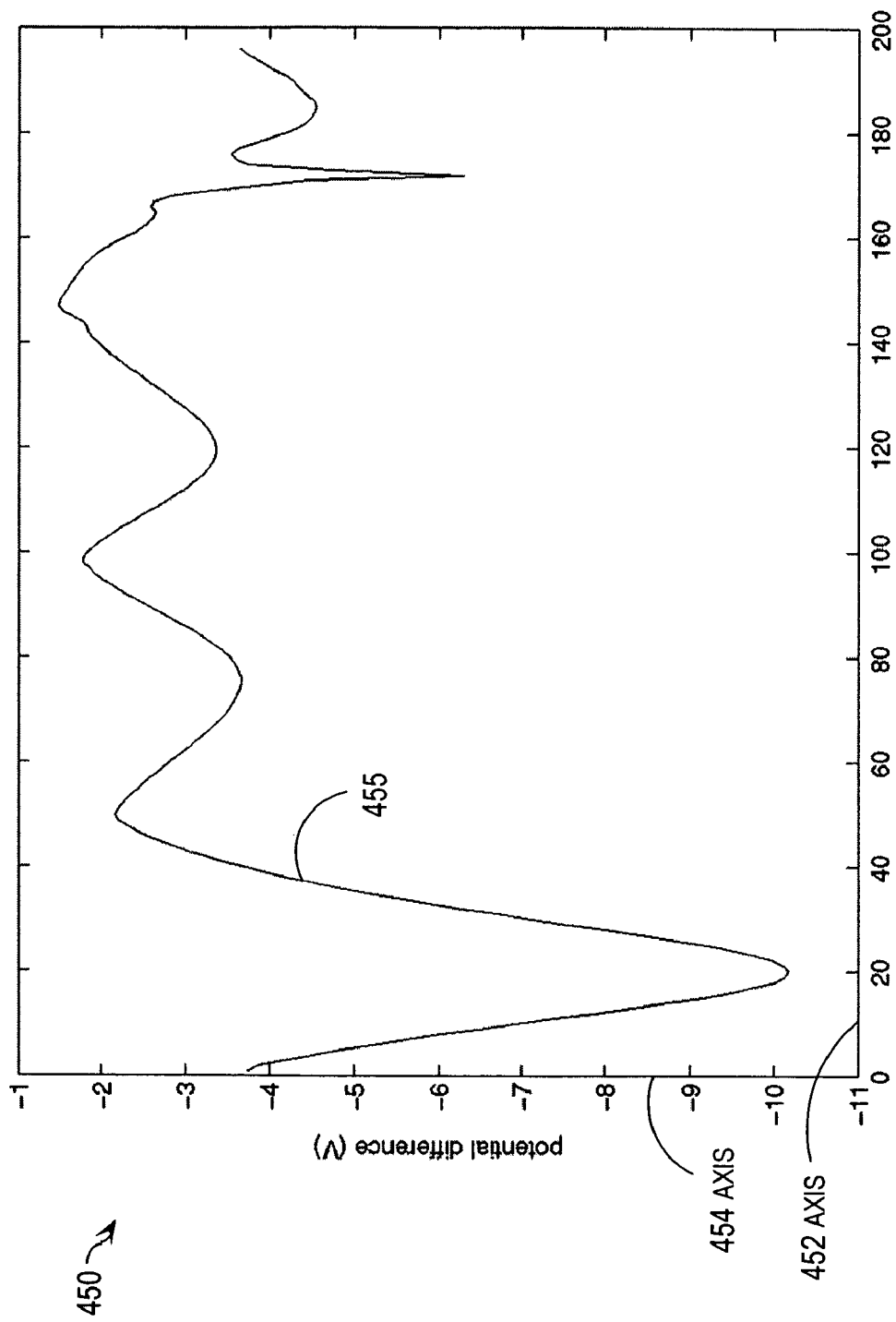
FIG. 4E is a graph that illustrates the signal along a perimeter of the region illustrated in FIG. 4A, according to an embodiment.

FIG. 4E is a graph 450 that illustrates the signal along a perimeter of the region illustrated in FIG. 4A. The axis 452 gives distance in arbitrary units along the perimeter of the walls; and the axis 454 gives signal strength (electric potential difference with and without dielectric targets) in milli-Volts (mV, 1 mV=$10^{31}$ $^3$V). The arbitrary distance may be thought of as an electrode number for the emitter and receiver electrodes—200 total electrodes with 50 electrodes positioned along each wall, although this in no way limits the functionality of the invention to scenarios were hundreds of electrode assemblies are used. For example, accurate reconstruction of dielectric target positions have been achieved with electrode assemblies spaced every 2 or 3 meters. Wall 411 is represented by the perimeter distance range 0 to 50, wall 412 by the range 50 to 100, wall 413 by the range 100 to 150, and wall 414 by the range 150 to 200. The source position along wall 414 is at perimeter distance 172. Plotted on graph 450 is curve 455 that indicates signal strength along the perimeter.

As is clearly seen in FIG. 4E, the signal has a strength of several milliVolts, well within the capability of available electric potential measurements. As mentioned above with reference to FIG. 4D, the maximum signal occurs along wall 411 where cylinder 431b comes closest to any wall. Smaller signals of similar magnitude to each other are evident on the walls 412, 413. The effect of the source along wall 414 on the signal is seen at the spike in the signal at perimeter distance 172. These simulations demonstrate that a readily measurable signal is available at the outside perimeter of building sized spaces for inferring the distribution of dielectric targets inside a building.

3.1.1 Example Linear Inversion in 2-D

In this embodiment, imaging the region involves inferring a two-dimensional field resulting from one or more circles of real dielectric constant $\in$ that yields the two-dimensional electric potential depicted in FIG. 4C from the signal along the perimeter depicted in FIG. 4E. In addition, other signals similar to that depicted in FIG. 4E are used, each based on a different positioned electrode acting as a source. This inferring process relies on taking samples of the signal along the boundary (a simulation for making measurements at receiver electrodes) for each of several source positions and applying inversion methods. In an illustrated embodiment, Greens functions are used in the inversion method to deduce the electric potential on a grid inside the walls based on the signal measured on the perimeter. In this embodiment, the Greens functions are linearized, and a solution to a linear system of equations is obtained using singular valued decomposition (SVD), a well known technique.

Equation 6, a differential equation, can be expressed in an integral form to facilitate linearization by a perturbation expansion. Note that $\Phi$ is a function of the vector position x where the electric potential is observed (e.g., at the receiver electrodes) and the vector position x' of the source (e.g., the emitter electrode). The integral form is given as Equation 7a.

$$\Phi(x,x')=\Phi_0(x,x')+(1/4\pi)\int G_0(x,x'')A(x'')\nabla\Phi(x'',x')dx'' \quad (7a)$$

where A(x) represents the coupling of the electric potential with the medium at position x, a directional vector given by Equation 7b, $$A(x)=\nabla \ln \in \quad (7b)$$

$G_0(x,x')$ is a distance factor given by Equation 7c for three dimensions (3-D), and by Equation 7d for two dimensions (2-D):

$$G_0(x,x')=1/|x-x'| \quad (7)$$

$$G_0(x,x')=2\ln[r0/|x-x'|] \quad (7d)$$

where r0 is a reference radius where the two dimensional potential is zero. The lowest order electric potential $\Phi\tilde{}_0(x, x')$ is given by equation 7e:

$$\Phi_0(x,x')=G_0(x,x')q/4\pi\in_0\in_S \quad (7e)$$

where q is charge in Coulombs in 3-D and charge density in Coulombs/m in 2-D, and $\in_S$ is the dielectric constant of the medium in contact with the source (e.g., the emitter electrode). In one embodiment, the lowest order solution represents the solution with the source present and no dielectric discontinuities such as walls or dielectric targets.

The perturbative expansion uses $\Phi\tilde{}_0$ inside the integral of Equation 7a to obtain a first order solution $\Phi_1$ for $\Phi(x,x')$. The expansion uses the first order solution $\Phi_1$ to obtain a second order solution $\Phi_2$, and so on until enough terms are included that the remaining terms are expected to contribute negligibly to the solution.

The measured signal is the difference between the high order solution for the case with dielectric targets and the solution without the targets. For example, in a case without walls, the solution without the targets is the solution with only the source, given by $\Phi_0(x,x')$. In this case the signal, represented by g(x,x'), is given by Equation 8a.

$$g(x, x') = \quad (8a)$$
$$\Phi(x, x') - \Phi_0(x, x') = (1/4\pi)\int G_0(x, x'')A(x'')\nabla\Phi(x'', x')dx''$$

which is recast for a discreet grid as $$g(x, x') = (1/4\pi)\Sigma_{x'}G_0(x, x'')A(x'')\nabla\Phi(x'', x')\Delta x'' \quad (8b)$$

In a case with walls, the signal is the measured potential $\Phi(x,x')$ minus the potential due to the walls and source only.

The positions of the charged sources x' are the positions of the various electrodes that serve as emitters, and the positions of the signal measurements x are the positions of the various electrodes that serve as receivers. The search region is divided into N cells of size $\Delta x''$. The position of each cell is x''. For each cell in the discrete grid, and for known positions of the electrodes, the values of $G_0$ and $\Phi_0$ can be evaluated as they depend only on the source, receiver and cell positions. (These quantities are fixed and precomputed in fixed geometry approaches.)

Equation 8b can be expressed in linear algebra form as Equation 8c $$g = K_A A \qquad (8c)$$

where g is an M×1 array of measured signals, where M is the number of measurements from the receivers and the emitters, A is a N×1 array of vectors, each vector including the directional gradient of the log of the dielectric constant as given above in Equation 7b, and $K_A$ is a M×N sensitivity matrix of vectors that represent the factors that depend on position of emitter, receiver and cell for each direction In an alternative approach, Equation 8b can be expressed in terms of the scalar quantity $\gamma$, given by Equation 8d $$\gamma(x'') = \ln \in (x'') \qquad (8d)$$

In this case, equation 8b is modified to the form given in Equation 8e $$g = K_\gamma \gamma \qquad (8e)$$

where $\gamma$ is a N×1 array of scalar quantities, $K_\gamma$ is an M×N sensitivity matrix of scalar quantities, and g is an M×1 array of measurements. The problem size is reduced from that represented by Equation 8c because each cell is represented by a scalar quantity rather than a vector of two quantities for 2-D or three quantities for 3-D.

Because equations 8c, 8e are linear in A, □, respectively, the sensitivity matrix K can be evaluated separately. Numerical integration to determine the elements of K is facilitated by the normalizations given by Equations 9a, 9b, 9c:

$$g^* x = K^*_{x,x'} \gamma_{x''} \qquad (9a)$$

$$g^*_x = g_x (2\pi)^2 \in_0 \in_S / q \Delta x'' \qquad (9b)$$

$$K^*_{x,x'}{}'' = (x''-x')(x-x'')/(|x''-x'|2|x-x''|2) \qquad (9c)$$

For each measurement of electrical potential at receiver electrode position x from an emitter electrode at position x', one row of the sensitivity matrix is computed using Equation 9c for the multiple positions x'' of the N cells in the search region. The sensitivity matrix K is highly singular.

Equation 9a is solved using singular valued decomposition (SVD) a procedure well known in the art. The normalized sensitivity matrix K* is decomposed into the SVD format given by Equation 10a $$K^* = U S V^H \qquad (10a)$$

where U and V are unitary matrices, the superscript H represents the Hermetian conjugate, and S is a diagonal matrix with eigenvalues $\lambda$ arranged in decreasing order along the diagonal. To reduce the effects of noise, the matrix S is truncated by substituting zero for eigenvalues below a threshold value $\lambda_T$. The SVD solution is given by Equation 10b $$\gamma = V S^{-1} U^H g^* \qquad (10b)$$

This solution gives the dielectric constant in each of N cells of the search region (the image reconstruction) based on the signal g computed by differencing a measured electric potential outside the building with the electric potential computed for the building without targets.

Outer walls near the electrodes significantly affect the image reconstruction, so the solution with walls is computed and used as the lowest order potential $\Phi^\sim_0(x,x')$ in Equation 8a. Using this lowest order potential, an image is produced that generates relative maxima in dielectric constant at the positions of the two cylinders. In practical terms, the lowest order solution may not always be known precisely. However, it is reasonable to expect that the apparent location and material of outer walls to a building can be made available for computing the lowest order potential $\Phi^\sim_0(x,x')$.

Noise levels affect the image reconstruction. Other simulations have shown, however, that a judicious choice of the eigenvalue threshold value $\lambda_T$ reduces the noise effect and enables image reconstruction with up to about 15 percent noise. Even though an increased threshold smoothes out the maxima in dielectric constant, it still allows the location of the maximum to be determined precisely. A 15 percent noise level corresponds to a signal to noise ratio (SNR) of about 18 deciBels (dB).

The solution is sensitive to electrode placement, e.g., high precision in the values of x and x'. Simulations show that placement with about 1 centimeter accuracy may be needed in some embodiments that use the linearized Greens functions.

The solution is computationally demanding. The computational cost for the Greens function inversion is essentially the cost of the SVD method, which scales roughly with the cube of N, the number of cells. Reasonable solution times are achieved using 1600 cells to cover a 10 m by 10 m building at one vertical position. However, 40 times more power is needed to obtain solutions at 16 different vertical positions.

3.2 A Three-dimensional Embodiment

In this embodiment, imaging the region involves inferring the position of one or more three dimensional targets having a particular dielectric constant $\in_T$ such that the arrangement yields the several electric potential signals observed along an exterior surface of a walled perimeter of the region. This inferring process relies on taking samples of the signal along the exterior walled perimeter as measurements (obtained in these simulations by running an accurate model for the 3-D electric field) for each of several source positions, and applying inversion methods. In this section, the signal is the total electric potential, (i.e., the electric potential expected with walls but without the target is not subtracted). In an illustrated embodiment, an efficient analytical model is used to estimate the electric potential for an initial arrangement of the one or more known dielectric targets at known positions, and an iterative inversion method is used to adjust the number and locations of those targets until an estimated signal, based on the estimated electrical potentials produced by those targets at those positions, closely matches the measured signal.

3.2.1 Example Signal Strength in 3-D

The electric potential to be used as a simulated measurement is generated by solving the three-dimensional, non-homogeneous Poisson Equation (Equation 6) for multiple locations in the search region. A numerical solution is obtained using the boundary element method (BEM) well known in the art. This method solves a partial differential equation by dividing the complex geometry of the domain of interest into small elements on boundaries and solving integral equations to obtain electric potential at positions interior to those boundaries. In the illustrated embodiment, COULOMB, a commercial electromagnetic simulation software package based on the BEM is used to generate three-dimensional solutions for the electric potential at measurement locations. COULOMB is a commercial software package available from Integrated Engineering Software of Winnepeg, Manitoba, Canada. The COULOMB tool was validated by generating solutions that agree sufficiently closely with electric potential fields for which exact analytical solutions are known. The COULOMB solutions are thus used in the development of the embodiments to generate a proxy for the measurement signal that is inverted to deduce the properties of the dielectric targets.

A significant difference between 2-D electrostatic modeling and 3-D electrostatic modeling is the existence of an electrical ground (a "ground") often taken to have zero electrical potential. The presence of a ground completely alters the electric field distribution in a region of interest such as the search region near the ground. When the ground can be treated as an infinitely large plane, the field from a charged body can be modeled with a reflected image of the charged body (a "virtual" charged body). This makes the modeling of the field from a source electrode a multi-source computation.

The 2-D problem can be treated as a 3-D problem with translation symmetry in the perpendicular (vertical) dimension, as was done above. For example, a charge in two-dimensions is treated as an infinitely long line charge in three dimensions. The electric field produced by such a charge scales with distance r from the source as $1/r^2$. In three dimensions, the electric field scales with distance r from a dipole source as $1/r^3$. For similar reasons, the electric potential generated by a 2-D dipole scales as $1/r$, whereas the electric potential generated by a 3-D dipole scales as $1/r^2$. Countering this effect is the effect of a grounded target, which tends to produce signal levels higher than in the 2-D case because more electric field lines are attracted to the conductor and shunted to ground.

In the COULOMB simulations described here, a spherical source near a wall is modeled with more boundary elements per unit distance on a circular area of the wall near the source and with fewer boundary elements per unit distance on the rest of the wall. The size of the ground plane modeled in a building is chosen to be large enough to have negligible difference with a truly infinite plane. Because a large ground plane demands a large number of boundary elements, in many simulations an alternative modeling approach available in COULOMB is used. In the alternative approach, an anti-symmetry boundary condition is imposed that introduces virtual charges beyond the ground plane to produce zero potential on the ground plane. No boundary elements are demanded to describe the ground plane. This approach saves considerable computational time.

Many simulations were run with no walls to verify that the COULOMB tool gave results comparable to the known analytical solutions or the FEM solutions generated by the PDF tool in MATLAB.

Several simulations were performed with walls or floors or both to determine the signal strengths to be expected in three dimensions. Typically in the simulations, the source (e.g., the emitter electrode) is modeled as either a circular patch or a sphere of radius 0.05 m with its center at a height of 1.4 m above the floor and a voltage of 200 V. The walls, floors and ceiling all have a thickness of 0.3 m and a dielectric constant of 4, roughly that of concrete. Electrical ground is below the floor. The dielectric target is either a cylinder or a sphere with a dielectric constant of either $\in_T=80$ or $\in_T=10^6$. The simulated dielectric target is intended as a proxy for a human being at different electrostatic frequencies. A target cylinder has a height of 1.7 m and either touches the floor or floats above the floor. The radius of the cylinder or sphere is varied in different simulations. The position of a dielectric target in the room is given by the coordinates of the center of the sphere or by the coordinates of the circle at the bottom of the cylinder. The computed electric field is sampled (simulating measurements by receiver electrodes) at a height of 1.4 m on the exterior surface of the walls. In some simulations, the source is moved a few centimeters outside the wall. In some simulations, the floor is removed to allow the targets to be electrically grounded, or to be separated from ground by 0.3 m of rubber (with dielectric constant of 3.45) to simulate the sole of a shoe. The simulations all indicated measurable signals on the outside of the walls.

Figure 5A:
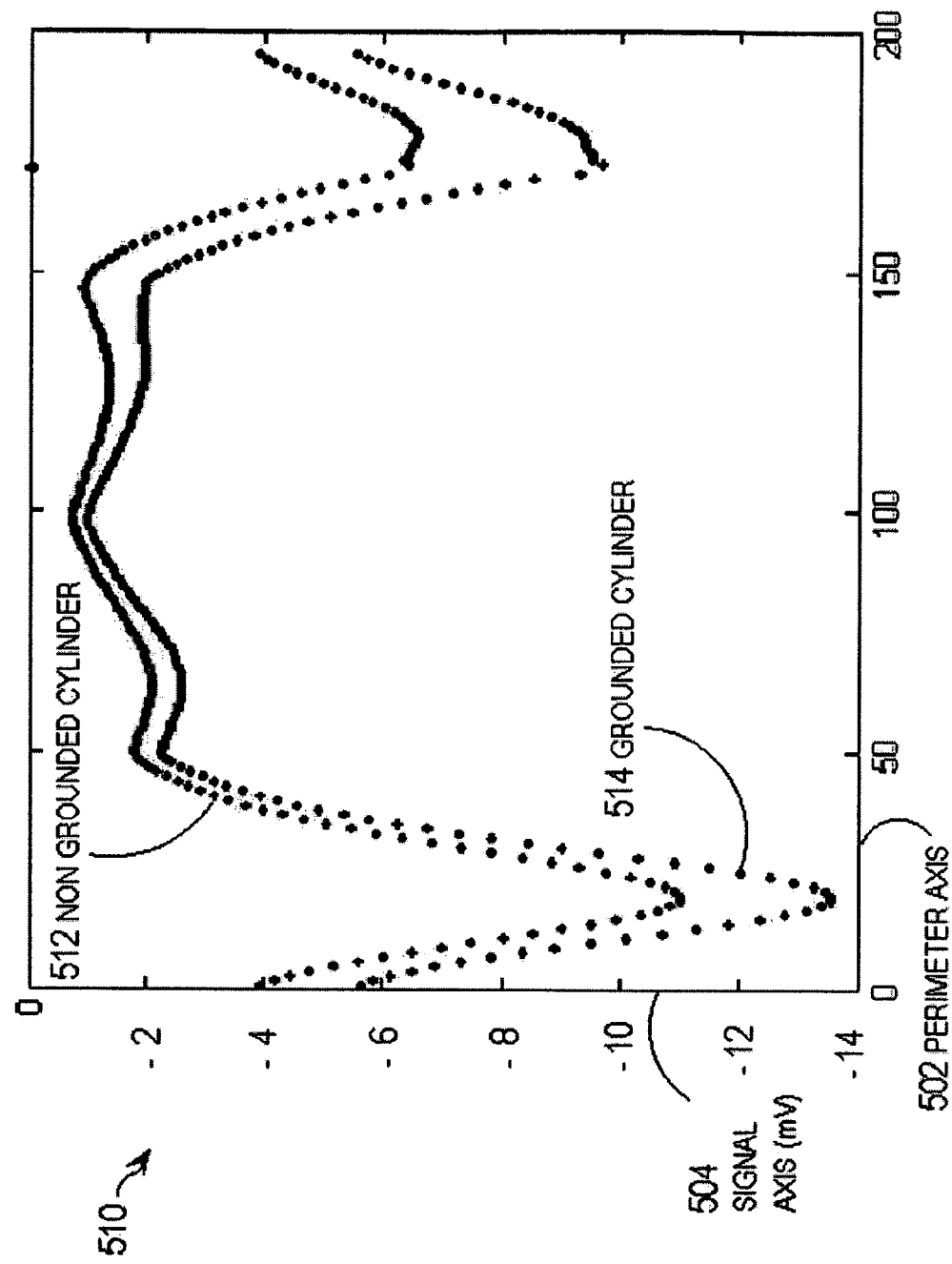
FIG. 5A is a graph that illustrates signals along a perimeter of the region based on three dimensional electrostatic simulations, according to an embodiment.
Figure 5B:
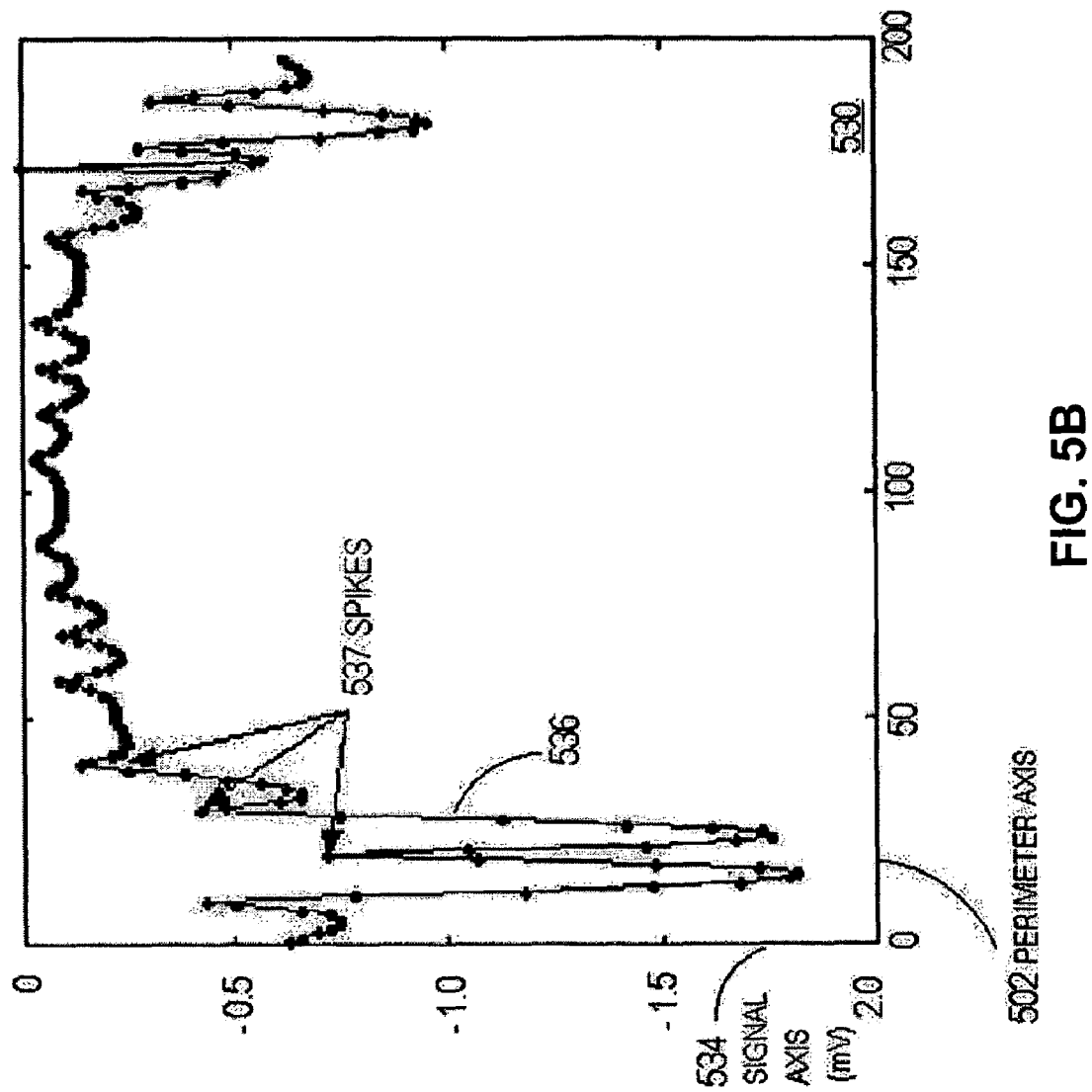
FIG. 5B is a graph that illustrates a signal along a perimeter of the region with metallic rods in the walls based on three dimensional electrostatic simulations, according to another embodiment.

For example, FIG. 5A and FIG. 5B show signals along a perimeter of the region based on three dimensional electrostatic simulations. FIG. 5A is a graph 510 that illustrates signals along a perimeter of the region based on three-dimensional electrostatic simulations, according to an embodiment. The axis 502 gives distance along the perimeter of the walls in terms of a sequence of measurement positions (e.g., receiver electrodes); and the axis 504 gives signal strength (electric potential) in milliVolts. The source position along wall 414 is at position 172. The walls define a search region that is 10 m by 10 m (as depicted in FIG. 4A) in the x and y dimensions, and 4 m high in the z dimension. Plotted on graph 510 is curve 512 indicating signal strength along the perimeter due to a single cylinder of radius 0.25 m located at (x, y, z) coordinate (7, 4, 0.03). This cylinder is not grounded. Also plotted on graph 510 is curve 514 indicating signal strength along the perimeter due to a grounded single cylinder of the same size and location.

Both signals are readily measurable with magnitudes of several milliVolts. Both show a maximum signal on wall 411 nearest the cylinder, with lesser magnitudes, approximately equal to each other, on walls 412 and 413, as described above for two dimensions. The signal for the grounded cylinder has a larger magnitude than the ungrounded signal because the grounding provides a charge source (or sink) for charges to move on or off the target. Therefore, the grounded cylinder carries a net induced charge. The ungrounded target simply redistributes a zero net charge on its surface.

The effect of the source at electrode 172 is evident as the data point with zero signal strength at position 172

FIG. 5B is a graph 530 that illustrates a signal along a perimeter of the region with metallic rods in the walls based on three dimensional electrostatic simulations, according to another embodiment. For this embodiment, sixteen (16) vertical metallic rods with radius of 0.02 m and height of 3.7 m are spaced uniformly along the four walls. Axis 502 is the same as in FIG. 5A. Axis 534 gives signal strength in milliVolts. Plotted on graph 530 is curve 536 indicating signal strength along the perimeter due to a grounded single cylinder of similar size and location as described above for curve 514. The signal strength for curve 536 is roughly ten times smaller than the signal strength for curve 514. This is consistent with the screening effects due to metallic elements. While the metallic rods are relatively widely spaced (2 m apart in the illustrated embodiment) the macroscopic (smoothed) characteristics of the signal clearly follow the signal for the embodiment without bars. There is a maximum signal on the wall 411 closest to the cylinder with lesser gradual extrema of about equal size on walls 412 and 413 and the effect of the source on wall 414. Even at tenths of a milliVolt, the signal strength is readily measurable with available technology.

The spikes 537 in curve 536 are located precisely where the metallic rods are embedded. This makes it possible to model the forward case again with metallic rods in the indicated positions. The clear detection of the spikes 537 suggests that receiver electrodes at the positions of the spikes 537 should be ignored, or moved to new positions between the spikes 537, or both. As the density of the metallic rods along the walls is increased, the overall shape of the signal is expected to converge to zero; and more spikes with reduced spike amplitudes will appear in the signal. This is expected eventually to reduce the signal below readily detectable levels as the structure behaves increasingly like a Faraday cage. In some embodiments, low frequency magnetic field measurements and inversion techniques are applied when behavior like a Faraday cage is encountered.

3.2.1 Example Iterative Inversion in 3-D

Rather than incur the computational costs and limitations of applying a linearized Green's function to infer a distribution of dielectric constant from measured electrical potentials in three dimensions, in an illustrated embodiment an iterative model based inversion method is applied. As described above, in an iterative inversion, a forward model that estimates the signal based on assumed positions of dielectric targets is repeatedly employed until some function of the difference between the estimates and the measurements is reduced to some acceptable level. This approach is also called a model matching method. It uses the solution of a constrained optimization problem whose variables include the size and position of the dielectric targets inside of bounded perimeters Any forward model may be used, including models based on FEM and BEM, described above. In an illustrated embodiment described below, a simplified analytical model is used as the forward model to substantially reduce the computational costs of applying the iterative inverse method. As shown below, the analytical model produces tactically useful estimates of the number and location of humans in a search region. The technique is shown to provide robust solutions that demonstrate a significant degree of immunity to noise, sensor position uncertainty, and sparsely populated measurements. The technique is not only computationally inexpensive, but also avoids imposing an explicit assumption of linearity.

The analytical model is based on the method of images. The assumptions include: 1) representing the interaction of one or more dielectric targets as finite charges; 2) using a conducting sphere (for which there is an exact analytic solution) as a proxy for a human; and 3) modeling the emitting source (the emitter electrode) as a sphere of constant potential.

A point charge in the presence of a ground plane can be treated using the method of images as a pair of charges with no ground plane. A virtual charge (an "image" charge) is located symmetrically with respect to the point charge using the ground plane as the axis of symmetry. The virtual charge has an equal but opposite charge compared to the point charge. The condition that the voltage is zero on the ground plane is a consequence of the arrangement of the point charge and its virtual image charge.

Figure 6:
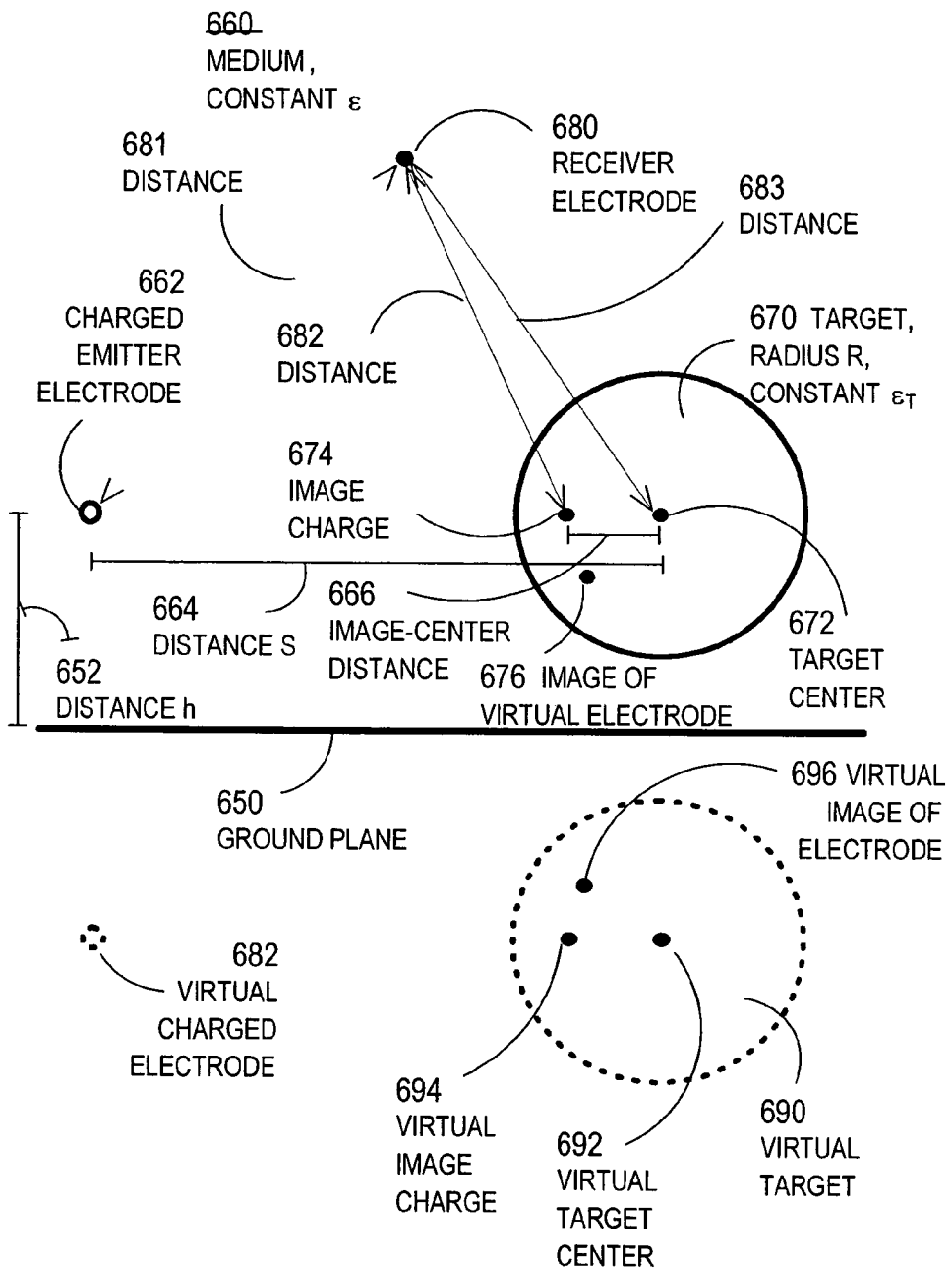
FIG. 6 is a block diagram that illustrates the image of point charges and virtual image charges for electrodes, a dielectric target and a ground plane, according to an embodiment.

The field due to point charge in the presence of a dielectric target can also be treated by the method of images. In this case, two image charges are necessary if the sphere is not grounded, but only one image charge is needed if the sphere is grounded. FIG. 6 is a block diagram that illustrates the point charges and virtual image charges for a dielectric target and ground plane, according to an embodiment. For purpose of shortening the following descriptions, the virtual image charges in the dielectric target are called image charges, while the additional virtual image charges introduced to maintain the ground plane are called virtual charges. FIG. 6 depicts a charged emitter electrode 662 that represents the point charge source, and a dielectric target 670 that represents an extended object with radius R, real dielectric constant $\in_T$, and a target center 672. In an illustrated embodiment, the charged electrode 662 and target 670 are shown in a vertical plane perpendicular to the horizontal x, y plane depicted, for example, in FIG. 4A. A horizontal ground plane 650 is present below the emitter electrode 662 and target 670. In the illustrated embodiment, target 670 is a conducting sphere with a real dielectric constant $\in_T$ appropriate for a conductor. In other embodiments, the target can have a different shape and a different dielectric constant $\in_T$. The emitter electrode 662 is a distance s 464 from the center of the target 670, and a distance h 652 above the ground plane 650.

According to the method of images, a source image charge 674 is located inside the target 670 at an image to center distance 666 from the sphere center 672 on a line connecting the center of the sphere to the emitter electrode. This image to center distance 666 is $R^2/s$ for a spherical target 670. For a charge q on the emitter electrode 662, the image charge is $-Rq/s$. If the spherical target 670 is not grounded, then a second image charge of $Rq/s$ is located at the center 672 of the spherical target 670, so that there is no net charge in the target 670.

Without a ground plane 650, the electric potential measured at a receiver electrode position 680 depends on the charge on the emitter electrode 662 and the distance 681 to the emitter electrode, the image charge 674 and the distance 682 to the image charge, and the charge, if any, at the center 672 of the target and the distance 683 to the center of the target.

To model a situation with a ground plane, a virtual charged electrode 682 and virtual target 690 are added symmetrically below the ground plane 650. The virtual charged electrode 682 induces an image virtual charged electrode 676 in the target 670. The virtual target 690 includes a virtual center 692 and images 694 and 696 of the virtual charged electrode 682 and the charged emitter electrode 662, respectively. If the target 670 is ungrounded with a charge at the center, then the centers 672 and 692 of the target and virtual target each have two charges, one for the emitter electrode 662 and one for the virtual charged electrode 682. Thus ten charges are modeled. The two charges located at each of the centers of the target 670 and virtual target 690 can be combined for a model with eight charges. The charges at the centers of the target 670 and virtual target 690 are not present if the target 670 is grounded—in which case a six-charge model suffices. In the illustrated embodiment, target to virtual target interactions are ignored. In some embodiments, the target to virtual target interactions are included.

In the illustrated embodiment, the analytical model assumes the emitter electrode 662 is a sphere with radius $R_S$ and potential $V_S$ at its surface. A sphere of constant potential is generated by a point charge at the sphere's center. This condition is achieved only approximately in the model due to the presence of the virtual charged electrode. The distance to the surface of the emitter electrode 662 from the point charge at its center is $R_S$. The distance $D_S$ to the surface of the emitter electrode 662 closest to the target 670 from the virtual charged electrode 682 is given by Equation 8a, using the Pythagorean theorem.

$$D_S = \sqrt{(4h^2 + R_S^2)} \qquad (8a)$$

Therefore the electric potential at this point on the emitter is given by Equation 8b $$V_s = \frac{q}{4\pi\varepsilon_0}\left(\frac{1}{R_s} + \frac{-1}{\sqrt{(4h^2+R_s^2)}}\right)^{-1} \quad (8b)$$

Solving for the charge q gives Equation 8c.

$$q = 4\pi\varepsilon_0 V_s\left(\frac{1}{R_s} - \frac{1}{\sqrt{(4h^2+R_s^2)}}\right)^{-1} \quad (8c)$$

The result expressed in Equation 8c gives the charge value desired to achieve the potential $V_S$ when there are no other charges present. However, a correction is used in order for the analytical model to more accurately predict the potential near the emitter electrode when dielectric objects are proximate. If the effect of the four or six charges are added, the result may be a reduction in the potential around the emitter electrode and, consequently, an insufficient ability to maintain a fixed potential at the emitter electrode. This is often referred to as "source loading."

A given source charge, qs, located at the source location xs, maintains a fixed potential $V_S$ at the measurement point $x_f$. The potential at $x_f$ due to a charge q at $x_s$ is linear. A proportionality constant $\zeta_d$ is selected, so that $V(q)=\zeta_d q$ results in the potential due directly to the charge q. Initially a charge $q_0$ is selected, resulting in a potential of $V(q_0)=V_S$ when the room is empty.

However, when there are one or more objects in an enclosed region, a charge q at $x_s$ gives rise to an induced charge distribution on the objects, which in turn alters the measured potential at $x_f$. This is also a linear phenomenon. The induced potential at $x_f$ due to a source charge q at $x_s$ is $\zeta_i q$. This means that when objects are introduced into the surveillance region, the necessary potential at the source is $V(q_0)=V_S+\zeta_i q_0$. This error can be corrected by adding a correction charge, $q_1$, to the source. This correction satisfies $\zeta_d q_1=-\zeta_i q_0$. The potential due directly to $q_1$ at $x_s$ is $\zeta_d q_1$, canceling the error caused by the induced charges. The $q_1$ term leads to another error: $V(q_0+q_1)=V_S+\zeta_i q_1$. The result is an infinite series of correction charges where the $i^{th}$ correction is given by $q_i=-(\zeta_i/\zeta_d)q_{i-1}$. Therefore the desired source charge is given by Equation 8d.

$$q_s = \Sigma_{i=1,\infty}q_i = \Sigma_{i=1,\infty}q_0\{-\zeta_i/\zeta_d\}^i = q_0/\{1+\zeta_i/\zeta_d\} \quad (8d)$$

Note that $\zeta_d q_0=V_S$. If $V(q_0)-V_S=\zeta_i q_0$ (i.e., the error in voltage potential, $\Delta V$, due to the original value of the charge), then the corrected source charge $q_s$ is given by Equation 8e.

$$q_s=q_0/\{1+\Delta V/V_S\} \quad (8e)$$

If left uncorrected, the measurements of the signal that are affected by nearby dielectrics loading the emitter electrode can significantly degrade the inversion process. For example, if the target is a single sphere of radius 0.75 m centered 1 m from the emitter electrode, the measurement error is above ten percent everywhere and reaches as high as seventy percent. In this example run, the value of $\zeta_i/\zeta_d$ is 0.033. As the target is separated more from the emitter electrode, the effect becomes smaller. For example, when a target sphere is three meters from the emitter electrode, $\zeta_i/\zeta_d$ is 0.00015 and the error due to loading is below 2 percent, except on the wall with the emitter electrode. When the target is near the center of a 10 m by 10 m region, the correction factor $\zeta_i/\zeta_d$ is 0.000009, and only four receiver electrodes near the emitter electrode exhibit an error over 10 percent if the corrective factor is not applied.

The analytical model gave good results when compared with COULOMB for one or more spheres, at considerably less execution time. The illustrated analytical model accurately estimates the electric potential from COULOMB at an arbitrary point on the boundary of the region for either free or grounded conducting spheres and a spherical source. The illustrated analytical model also gave exceptional agreement with COULOMB for a sphere with $\in_r=80$, even though the analytical model uses the closed form for a conducting sphere.

Note that in two dimensions without a ground plane a similar analytical model can be used. In such a 2-D analytical model, the emitter electrode 662 is a line charge perpendicular to the 2-D plane, the dielectric target 670 is a cylinder with circular cross sectional area in the 2-D plane, and the ground plane 610 and virtual target 690 and virtual charge 682 are omitted.

Let v be a vector of parameters, such as sphere position in three dimensions and sphere radius for one or more spheres. Let E(v) be the analytical model's estimate of the signal for the vector v, and S be the measured signal (e.g., as simulated by COULOMB). The model matching procedure attempts to estimate the vector v*, given by Equation 9.

$$v^*=\text{argmin}_v \log|E(v)-S| \quad (9)$$

This approach minimizes the mean square error of the analytical model's estimate E(v). The logarithm does not change the value of v*, but it does affect the convergence of the solution. In other embodiments, other objective function formulations are used to locate the absolute minima of the typography corresponding to the correct solution. The recovered target horizontal position portion of v* is constrained to lie inside the search region. The height and radius portion of v* are constrained to be positive values. The resulting constrained nonlinear optimization problem is solved using the MATLAB™ Optimization Toolbox using a Sequential Quadratic Programming (SQP) method. In an illustrated embodiment, the measured signal S used as input to the SQP method consists of electric potential at 49 points on each wall (e.g., representing receiver electrodes at 0.20 m spacing) with nine emitter electrode positions (each emitter electrode position separated by 1 m) on each wall. This gives a total of 7,056 measured electric potential values. Thus not all electrode assemblies are used as both emitter electrodes and receiver electrodes; only about 20% of the electrodes are used as emitter electrodes.

For example, when 7,056 COLOUMB electric potential values are provided for a conducting sphere of radius 1 m at (x, y, z) coordinates (9, 8, 5), and an arbitrarily selected starting position of (5, 5, 0.3) and starting radius of 0.25 m are used, the SQP method yields a v* indicating a radius of 1.0000 m at (9.0000, 8.0000, 5.0000)—a perfect result. When 7,056 COLOUMB electric potential values are provided for a conducting sphere of radius 0.6 m at (x, y, z) coordinates (6, 4, 2), and an arbitrarily selected starting position of (7, 7, 0.3) and starting radius of 0.25 m are used, the SQP method yields a v* indicating a radius of 0.6000 m at (6.0000, 4.0000, 2.0000)—another perfect result. Single targets without walls consumed about 60 to 70 model iterations to successfully converge.

The illustrated inversion method is demonstrated using COULOMB to generate electrical potential proxy measurement data and using the illustrated analytical model to determine the position and radius of spheres that best matched that data. In various simulations, the COULOMB data was generated using both spheres and cylinders as proxies for humans in un-walled and walled regions. The matched model solutions provided the location and radius of conducting spheres that best matched the measurements from the COULOMB model. Model matching that yields spheres that are too unlike the spheres serving as a proxy for a human indicate a situation in which it is unlikely that a human occupies the region.

The inversion formulation is also demonstrated for multiple targets. The model driven inverse formulation demonstrated an ability to accurately converge to target position solutions. In one example two target objects (spheres with radii 0.5 meters and 0.4 meters respectively) were placed at (3, 4, 1) and (7, 6, 0.8). The algorithm correctly converged to two solutions at (3.0000, 4.0000, 1.0000) and (7.0000, 6.0000, 0.8000) with radii of 0.5000 meter and 0.4000 meter. The objective function value is −15.5 for the two-sphere case. If the signal for two spheres is processed to find a single object an objective function value of −2.9 is obtained: there is no ambiguity between one target or two targets.

The method is robust against uncertainty in the number of targets. Simulated measurement data for a single target of radius 0.6 m located at (6, 4, 2) was input into the analytical model based inversion algorithm with initialization values for two target objects. The algorithm correctly converged to a single target object solution with an objective function value of −15.2 whereas the two-sphere solution obtained had an objective function of −4.8; it is clear that the one-sphere solution is better. From these results it appears that the inversion algorithm is capable of readily distinguishing between one and multiple targets.

The illustrated embodiment experiences more variability when there are multiple targets, depending on the initialization point used for the optimization algorithm. The selection of initialization values is a design choice that impacts the performance. It is noted that imperfect information may still be tactically useful. For example, it may be tactically sufficient to know that there are more than four persons in a room or building without knowing whether there are exactly five persons or exactly six persons.

The illustrated embodiment continues to perform usefully under various more difficult circumstances, as simulated below. For a single cylinder located at (x, y, z) coordinates (7, 4, 0.3), the analytical model matched the data with a sphere of radius 0.6173 m at (7, 4, 0.571). Raising the height of the spherical emitter electrode from 1.4 m to 2.5 m and lowering the cylinder to a z coordinate 0.01 m above the ground plane also produced close matches, e.g., a sphere of radius 0.6512 m at (7, 4, 0.0154). For a cylinder at (1, 2, 0.3) the analytical model matched the data with a sphere of radius 0.5765 at (1, 2, 0.6674). Moving the cylinder horizontally at the same height changed somewhat the radius and height of the sphere matched by the analytical model. For two cylinders of radius 0.25 m and height 1.7 m at coordinates (1, 2, 0.3) and (7, 8, 0.3) the analytical model matched conducting spheres of radius 0.5747 m at (1, 2, 0.6651) and radius 0.7065 m at (7, 8, 0.8439). For two closely space cylinders at (7, 4, 0.3) and (4, 6, 0.3) the analytical model matched conducting spheres of radius 0.61 m at (7, 4, 0.5487) and radius 0.68 at (4, 6, 0.6367).

The illustrated analytical model embodiment also performs well when matching potentials for targets enclosed in regions with dielectric walls or floor. For a cylinder of radius 0.5 m at (7, 4, 1) over a dielectric floor, the analytical model matched the data with a conducting sphere of radius 0.4128 m at (7, 4, 0.7791). For a cylinder enclosed in dielectric walls, the analytical model match without walls is better away from the emitter electrode or when the target is grounded. The analytical model matches COLOUMB data for cylinders enclosed in walls adequately to locate cylinder targets in two dimensions.

In general, exact matches are not expected to be required to obtain tactically useful information. The absence of human proxy spheres, or the presence, number and location of human proxy spheres that approximate the actual number and locations of humans in the region is likely to be tactically useful information.

3.3 Selective Placement

The location for the emitter and receiver electrodes demonstrates a favored collection geometry, in the illustrated embodiment. The emitter electrode height (z coordinate) should be chosen above the estimated or nominal height of the dielectric target by perhaps 50 percent. This suggests that electrode location can be perturbed to enhance the accuracy of target position. In other embodiments, embodiment-specific sensor placement schemes can be determined. Further, in some embodiments electrode location can be autonomously perturbed to enhance the accuracy of target position.

The optimal collection geometry for the illustrated embodiment was demonstrated by solving an optimization problem that can be framed in two general ways. The first way is to select the emitter electrode position that maximizes the signal over the whole domain. The second way is to consider a parameterized location for emitter and receiver electrodes and identify the best parameters. For example, the emitter and receiver electrodes may be constrained to lie in a plane parallel to the ground.

Embodiments with mobility for electrode assemblies enable the network of sensors to be reconfigured to enhance either wide area surveillance or resolution in specific, high interest areas. For example, if a suspect area were observed on a preliminary scan, the sensors could be repositioned to aggregate at an optimal geometry to enhance resolution in the high interest region. In some embodiments, electrode assembly mobility is driven by human operators. In some embodiments electrode assembly mobility is adaptive, in that the sensor network uses a rule-based system to perturb its spatial configuration to enhance performance, e.g., to minimize dilution of precision, minimize ambiguities in target object position or second order characteristics, or optimize the information content of data measurements, or some combination of these.

3.3.1 Height of Emitter Electrodes

In the illustrated embodiment, the optimal emitter electrode height for the analytic model inversion was determined by evaluating 9,800 measurement points at heights ranging from 0.2 meter up to 10 meters. The $L_2$ norm of the resulting data vector (i.e., the square root of the sum of the squares) was computed and taken to be a measure of the signal strength. Optimal height for the emitter electrode means that the measured signal $L_2$ norm is maximized by placing the emitter electrode at that height.

Signal strength was plotted as a function of emitter electrode height. Each plot showing source height as a function of object height involved 2,208 model evaluations. When the target is at (7, 4, 2) and the emitter electrode is at (5, 0), the optimal height for the emitter electrode is found to be at 3 meters, 50 percent higher than the height of the target. As the target moves farther from the ground plane, the effects of the ground plane diminish and it is optimal to have the emitter electrode at the same height as the target. When the target is at (5, 5, 2) the optimal height for the emitter electrode is 2 meters.

Once the target reaches a critical height, slightly below 3 meters in the illustrated embodiments, the optimal emitter electrode height is equal to the target height. But for lower target objects, greater emitter electrode height yields increased signal strength and reduced signal to noise ratio (SNR). This type of behavior appears to be related to the location where measurements are being taken, namely on four orthogonal walls. When the emitter electrode nears the walls, a non-monotonic relationship is observed between target height and optimal emitter electrode height.

Optimal source height was demonstrated for various emitter electrode-target pairs which are the same distance apart (on the two dimensional plane). Several assumptions were made to facilitate this demonstration. First the emitter electrode was moved from (5, 0) to (9, 0) in steps of one meter. For each emitter electrode position considered, the target or targets are located a fixed distance, d, away from the emitter electrode—either vertically or along two directions at 45 degree angles from the wall. Lastly, only targets that lie inside the 10 m×10 m structure were considered as valid solutions.

The relationship between optimal emitter height and target height was demonstrated for the illustrated embodiment where the distance to source (d)=2 m. Outliers occur when the source is at (8, 0) and the target object is at (9.4, 1.4). The remaining plots are tightly bundled together and show that once the target reaches an altitude of 2 meters, the emitter electrode is best positioned at the same height as the target.

The relationship between optimal emitter height and target height were plotted for distance to source (d)=4 meters. Once the target height attains 4 meters, the pattern reliably converges to indicate that the emitter electrode height equals the target height. For the distance to source d=8 meters, the solutions still maintain the same general relationship to emitter electrode height, but the data is more noisy and the optimization due to electrode height is less clear.

In summary, assuming 360 degree coverage of the building structure, e.g., for electrodes located on each external wall, a target that is far from the emitter electrode located on one wall will in turn be near the emitter electrode on the other opposite side of the structure. When the target is farther away, it yields a smaller signal so it is more important to optimize for the near case. To detect low (i.e., vertically depressed) targets, the emitter height should be chosen above the estimated or nominal height of the target by perhaps 50 percent.

3.3.2 Horizontal Position of Receiver Electrodes

Because the analytical model error is largest around the emitter electrode, the effect of moving receiver electrodes away from the emitter electrodes was also demonstrated for the illustrated embodiment.

In this demonstration, a grounded conducting cylinder sits on the ground plane at (7, 4). When all of the data is fed to the inverse solver based on the analytical model, the resulting position estimate is (7.02, 3.86, 2.05) and the resulting radius is 0.20 meters. The arbitrary initial position was (5, 5, 0.5) and the initial radius was 0.25 m. The initialization parameters were varied, but the inversion algorithm still converged to the same solution.

When the 49 data points from receiver electrodes around the emitter electrode were discarded, equivalent to moving receiver electrodes to more distant walls, the inverse algorithm located this object at (6.78, 4.08, 0.77) with radius 0.67 m. If the height of the initial condition was increased to 1 m, then the inverse solution based on the analytical model converged to a solution at (6.81, 4.07, 1.02) with radius 0.54 meter. Discarding relatively noisy data from around the emitter, or moving receiver electrodes away from the emitter, does not appear to improve the accuracy of position recovered. On the other hand, eliminating measurements from electrodes near the source does not degrade the solution and benefits from using fewer computation and communication resources.

Restricting the sensors to one wall limits the range of the illustrated embodiment. In a first test case, the sensors are located only on Wall 412, opposite the emitter electrode, as shown in FIG. 4-A. Inputting the COULOMB derived voltage potential signal into the analytical model driven inversion is able to recover the x position of a single target. Using data from only one wall performed almost as well as it did when the receiver electrodes are placed on all of the walls for one coordinate. The x coordinate was computed as 3.86 using data on all four walls. With only Wall 412 data, a x value of 3.79 is found, when the SNR is 30 dB—only a slight decline in accuracy.

The y position, on the other hand, is significantly degraded with sensors on only one wall and totally dominates the computation of position error. In the baseline case, where data measurements from all four walls was assumed available and processed, the $\gamma$ position was estimated by the inversion algorithm to a 0.02 m accuracy (as compared to the position used to compute the simulated data measurements in COULOMB). With sensors on only one wall, the error was almost three meters for the case with a SNR of 30 dB.

The demonstration shows that for the illustrated embodiment with data measurements constrained to be on only one wall, the model based inversion is able to recover the position parallel to the wall but has limited success in the dimension perpendicular to the wall. This suggests that polling strategies based on the illustrated embodiment should employ receiving electrodes on more than one wall, when possible The case of sensors located on two orthogonal walls is also demonstrated. Specifically, sensors were located on Walls 411 and 412 as shown in FIG. 4A. For a single cylinder at (4, 7) the model driven inversion localizes the object to a position error of 0.2 m, nearly as well as with data from all four walls. Performance for the best initial condition out of ten shows a gradual degradation beginning at an SNR of around −5 dB.

While one of the solutions exhibits an increased position error at a lower SNR, in the other five solutions all the inversion solutions demonstrate the expected behavior of relatively small position error for relatively large SNR, with a rapid increase once a threshold is crossed.

3.4 Selective Processing

In some embodiments, the electrode assemblies constitute a natively netted sensor constellation; the data derived from any one sensor in the network can only be exploited and interpreted in the context of data from other sensors sensing the same object. A number of polling strategies are contemplated to equalize data throughput, minimize sensor and communication power, improve probability of detection, and enhance wide area surveillance and reconstructed image formation.

The simplest polling approach is a "round robin" protocol, where one sensor emits and every other sensor makes an electric potential measurement. Round robin polling was implemented in the inversion demonstrations described above. Round robin polling makes the highest demands on communication and computational resources as well as sensor power.

A modification of round robin polling elects a subset of sensors, which have measurements that are in spatial locations better suited for information content. For example, measurements from receiver electrodes proximate to the emitter electrode have relatively little information content; and thus these receiver electrodes are inhibited from taking part in the polling and subsequent processing. As another example, measurements from receiver electrodes on only two perpendicular walls are polled, excluding the wall where the emitter electrode is located, and including the non-emitter wall with the maximum signal.

Another polling strategy used in some embodiments inhibits all nodes from making measurements unless specifically enabled by the processor. A variation on this polling is an embodiment that exploits the mobility of the sensor nodes to dynamically reposition the constellation to enhance observability in high interest areas, as suggested above.

Computational requirements for many embodiments are expected to be high. Localization using the analytic model based inversion for one target object took an average 0.9 central processing unit (cpu) seconds per iteration on an Athlon 1.7 gigaHertz (GHz, 1 GHz=$10^9$ Hz) processor. For two target objects in the 10 m by 10 m search region, each iteration took an average of 2.5 cpu seconds. This leads to total run times ranging from about 45 seconds for a single target up to about eight minutes for an exceptionally long two-target run. The run time is dominated by the model evaluation of 7,056 data measurement values (sensors spaced about 20 cm) while the most computationally expensive step in the optimization is solving an 8×8 linear system of equations for the two target object case.

As the number of targets increases to N, this optimization method involves 4N variables representing the positions and radii of the N targets. Therefore the optimization will solve a 4N×4N system of equations at each step, taking on the order of $N^3$ operations, $O(N^3)$. At each step the model will be evaluated O(N) times and the model computation also scales as O(N), so model evaluation will require $O(N^2)$ time. Therefore for very large N the cost of optimization iteration scales as $N^3$. However, for all the N values of practical interest it is expected that the model evaluations will dominate the calculation as is the case for N=1 and N=2, and in this regime the run time for a single iteration depends quadratically on N. However, processing for other, second order effects (e.g., target object size, shape and orientation) could require significantly more computational resources, even with highly optimized algorithms.

Both distributed and centralized processing implementations are contemplated. In some embodiments, at least some signal processing takes place on the electrode assemblies, e.g., noise filtering, data filtering and averaging (if a coding scheme is employed to enhance SNR and operational range) and possibly adaptive control of the measurement reference (e.g., electrical ground). The analytical model for inversion described above does not readily lend itself to parsing for parallel or distributed processing. However, it is anticipated that different processing schemes used in other embodiments would be amenable to distributed processing.

A factor that could serve to significantly mitigate the processing requirement is to limit the number of data measurements N. This possibility was tested by reducing a measurement data set collected every 0.20 m by various factors. A decimated data set enabled recovery of the position of a single target object with a position error of 0.15 meter. The complete data measurement set exhibits less error, between 5 dB and −20 dB better, and both methods degrade as the SNR worsens. The demonstrations indicate that, for the illustrated embodiment, reducing the number of data points impairs the resistance of the inversion algorithm to noise, but good results are possible with many fewer data points than the number used in the above demonstrations. For two widely separated target objects, 90 percent of the data measurements could be discarded and yet the algorithm still converges to correct target positions with root mean square (RMS) errors of 0.2 m and 0.45 m, respectively.

3.5 Spectroscopic Detections

The illustrated embodiment exploits external measurements of electric potential made along the boundary of a search region to characterize or identify the detected dielectric.

The frequency dependent real dielectric properties of humans are significantly different than the dielectric properties of inorganic materials. In some embodiments, the measurements used to detect and image the region are further exploited to at least differentiate humans from non-animate objects. The dielectric properties of biological media exhibit strong dispersion in the 1 kHz to 1 MHz frequency range. In a one embodiment, this dispersion is used to distinguish biological, inanimate, and metallic media in closed structures based on electric potential measurements made on the exterior surface.

A series of papers compiled the existing data on the dielectric properties of biological tissues and parameterized the data to fit a multiple Cole-Cole dispersion function. See S. Gabriel et al, "The dielectric properties of biological tissues: I, II and III", *Physics in Medicine and Biology*, Vol. 41, pp. 2231-2293, November 1996 (hereinafter, Gabriel), which is incorporated by reference herein in its entirety. The Cole-Cole dispersion function provides a vehicle to transform basic material parameters, such as dielectric constant and conductivity into a complex impedance graph with the real and imaginary parts of the impedance plotted as a function of frequency.

As shown by Gabriel, the dielectric properties of blood are a strong function of frequency. At particular frequencies, the dielectric constant decreases with a corresponding increase in the dielectric loss. There is a large relaxation at 100 kHz, in which the dielectric constant decreases from 9,000 to about 80. This large change in the dielectric property of blood results in a significant impedance change. In addition, the high dielectric constant of blood at frequencies between 10 Hz and 100 kHz makes blood easily distinguishable from non-conducting materials such as plastics, wood and metals. For example, most plastics have a dielectric constant between 2 and 4 in the 10 Hz to 100 kHz frequency range.

A human body is taken as a cylinder of 1.8 m height with a radius of 0.6 meter, giving a total volume of a human ≈0.14 m³. Table 1 summarizes the resulting permittivity and conductivity of a generic human modeled as a parallel connected component at three frequencies 1 kHz, 100 kHz and 1 MHz.

TABLE 1

Human Body Permittivity and Conductivity Variation with Frequency

| | 1 kHz | 100 kHz | 1 MHz |
|---|---|---|---|
| $\bar{\epsilon}_{human}$ | $69 \times 10^5$ | $1.7 \times 10^4$ | $8.1 \times 10^3$ |
| $\bar{\sigma}'_{human}$ $(\Omega m)^{-1}$ | 0.21 | 0.21 | 0.21 |

Six humans in a structure measuring 10 m×10 m×4 m, would make up a volume fraction of 0.0022 of the enclosed region; however, the vertical position of the humans in the search region can be constrained to $0 \geq z \geq 2$ meters. This constraint increases the volume fraction of humans embedded in the search region. The dielectric constant and conductivity of air are $\epsilon_{air} \approx 1.0$ and $\sigma_{air} \approx 1.0 \times 10^{-5}$ respectively. Thus the effective permittivities of the region with the embedded humans for 1 kHz, 100 kHz and 1 MHz are computed and summarized in Table 2.

TABLE 2

Effective Permittivity of Test Region with Embedded Humans

| | 1 kHz | 100 kHz | 1 MHz |
|---|---|---|---|
| $\bar{\epsilon}_{eff} \rightarrow$ 1 human | 1.0053 | 1.0033 | 1.0029 |
| $\bar{\epsilon}_{eff} \rightarrow$ 3 humans | 1.0161 | 1.0099 | 1.0089 |
| $\bar{\epsilon}_{eff} \rightarrow$ 6 humans | 1.034 | 1.021 | 1.019 |
| $\bar{\sigma}_{eff} (\Omega m)^{-1}$ | $1.02 \times 10^{-5}$ | $1.02 \times 10^{-5}$ | $1.02 \times 10^{-5}$ |

The real part of the dielectric constant of the humans vary about two percent over three decades of frequency for the assumed search region. Significantly, the change in dielectric constant over these same three decades of frequency is about 0% for metals, plastics, and many other non-organic material. According to some embodiments, this difference in frequency dependence provides the basis for an effective filter to differentiate targets detected in a search region. Additional work can analytically estimate and verify by empirical measurements the actual relationship between a variety of non-organic materials and their rate of change with respect to frequency compared to humans.

3.6 Processing for Noise

Here the degree of susceptibility to environmental noise, uncertainty in the knowledge of the sensor positions, and noise due to inconsistent electrical ground reference is demonstrated for various embodiments.

The model driven inversion approach is able to locate objects behind walls to a varying degree of accuracy with horizontal position errors in the noise free case ranging from 12 cm to about 80 cm. The approach is robust both to electrode position error and to noise. Noise levels to an SNR of 0 dB seem to present little trouble, and random perturbation of measurement locations with a standard deviation of a $\sigma=0.4$ m can be tolerated. If the exterior surface of the structure is constrained such that sensor measurements are limited to two sides of the structure, the operational range of the system is apparently reduced (for an emitter electrode maintained at 200 V). Convergence varies somewhat with the selection of starting positions for the parameter vector v. A best solution is obtained by using several starting positions and selecting the solution with the best fit. Better tuning of the optimization algorithm or investigation of the starting point choices should lead to improvements in selecting the starting locations.

Atmospheric noise levels are frequency and geographically dependent. Mean noise power values are given as dB above $kT_oB$ (k is Boltzmann constant, $T_o$ is 290K and B is the system bandwidth), and values range from approximately 30 to 70 dB at a frequency of 1 MHz over landmasses. Inspection of noise maps shows that a value of 60 dB is a conservative estimate over much of the globe. Environmental noise varies as approximately $f^n$ where n varies from 2 to 3—implying a noise power of approximately 90 dB (above $kT_oB$). Assuming a voltage sensor couples to free space as an antenna, and assuming a free space impedance of 377 ohms, about 1 mV of noise power is estimated. At such levels, the analytic model based inversion produces a target position with a RMS error of about 0.13 meters. If the noise level were increased to a standard deviation of 10 mV (resulting in an input signal with a SNR of −8.6 dB) the target object position was recovered with a position error of only 0.27 m. As the noise level increase to noise level higher to an SNR of −22.6 the inversion still converged but to an approximate target position with a position error of 1.3 meters. Thus simulations show a relative insensitivity to environmental noise.

Another possible source of noise is uncertainty in the estimate of sensor position. To quantify this effect the location of the sensors (spaced at 0.2 m intervals) in the model were perturbed by Gaussian white noise to a sensor location standard deviation of σ. When the sensor locations are perturbed by white Gaussian noise with a $\sigma=0.1$ m, the position of a single cylinder was recovered with a position error of 0.1 meter. When a $\sigma=0.5$ m the target position estimate degraded with a position error of 0.7 meters. Only at $\sigma=0.1$ m did the inversion fail to converge to a solution. These results suggest a substantial insensitivity to error in sensor position. At a standard deviation of 0.5 meter, more than half the data has been perturbed beyond the next sensor's nominal location. Perturbing the height only of the source by noise with $\sigma=0.1$ meter also gives good results with a position error of 0.16 meter. The inversion algorithm shows relative insensitivity to sensor position error up to about a $\sigma=0.4$ meter The noise due to inconsistent or variable electrical ground is also considered. The ultimate goal in some embodiments is to take physical voltage measurements on the exterior of a building structure and exploit the measurements in a robust inversion technique. Signal levels are of order milliVolts, so it is beneficial to constrain the error in the ground potential to which the measurements are referenced. A preliminary assessment is that there needs to be a common "ground" for emitter and receiver electrodes to eliminate differential biases and variances between measurements. A physical approach to providing a common ground reference could be to tie all "low side" wires (source and sensor) to a common physical point such as true ground or soil. Two or more spatially separated grounding positions may be used provided that the resistance between the locations is accounted for.

Typically, soil conductivity ranges from 0.001 to 0.01 mhos/m. The physical separation of low side wires of 20 meter and a conduction area on the order of meters squared has resistance of order tens of kilo ohms; which can be tenths of a percent of the receiving electrode's input impedance. If the physical arrangement for the target/no target case is identical, each set of perimeter voltages will be offset from the "true" perfect common ground values, and the voltage difference signal is likely not corrupted. The difficulty arises in guaranteeing uniformity for the measurements. A one percent variation in a nominal grounding resistance of 10 kilo ohms using a 10 mega ohm voltage sensor and nominal 100 volt perimeter value, yields about a milliVolt variation. As set forth above, 1 milliVolt error is acceptable and will probably not degrade image reconstruction. However, the bias and variance due to multiple ground references (or no reference) could significantly degrade image reconstruction. Some embodiments address this issue by digitally referencing the analog measurements.

3.7 Hardware Components

The hardware components for embodiments do not stress the state of the art. The electrostatic tomography envisioned in some embodiments requires a source with controllable voltage output and frequency. The nominal emitter electrode employed in the illustrated embodiments was a 200 V source operating at a frequency between 1 kHz and 1 MHz. The nominal current needed to hold the emitter electrode at a fixed potential varies between 7 microAmperes ($\mu A$, 1 $\mu A=10^{-6}$ Amperes) at 1 kHz to 7 milliAmperes (mA, 1 mA=$10^{-3}$ Amperes) at 1 MHz. For dielectric objects proximate to the emitter electrode, source loading increases the emitter electrode current requirement to hold the emitter electrode at a fixed electric potential. When the dielectric object gets very close to the emitter electrode, the correction factor can become significant. Assuming an emitter electrode that is a sphere of radius 0.19 m located with its surface 0.01 m from a dielectric wall, an increase in current flow of 17 percent is predicted. If the same emitter electrode were located so its surface was 0.10 m from the wall, then an 11 percent increase occurs. Still, the defining parameters of voltage, current, and frequency are readily realizable using commercial components.

Numerous vendors supply components that can be used to generate a controllable alternating electric field and sense electric potentials. Estimated receiver electrode sensitivities ($\mu Amp$) are not beyond the state of the art and a number of engineering designs could be explored. Many available source and sensor designs are available in small form factors (e.g., on the order of 1 $cm^2$). For example, at the time of this writing, Motorola, Inc. of Chicago, Ill., recently announced a single integrated circuit (IC) that both generates and detects a low-level electric field (e-field) and powers and supports a microcontroller. Motorola reports that the MC33794 chip has been "designed to . . . provide information on the size or location of an object in a weak electric field." The immediate market for the electrostatic sensing integrated circuits (IC) is the automotive industry. The electronic safety system producer of Elesys North America, Inc. (formerly NEC Technologies Automotive Electronics Division) has incorporated the MC33794 in its SeatSentry occupant-sensing system to suppress airbag deployment for out-of-position occupants. The system generates low-level electric fields from multiple sensing electrodes fixed in the seatback cushion to identify a child or small adult by source loading. Like the source contemplated for some embodiments, the MC33794 generates a high purity sine wave optimized for 120 kHz and measures the resultant field coupled onto the non-driven electrode(s). It can be programmed according to embodiments described above to interpret the resulting data and make a determination of an object interfering in that field. Manufactured with Motorola's SmartMOS process, the IC device has a functional range of 1 cm to 10 cm. The MC33794 is housed in a 44-lead package and is currently available in sample and production quantities at $3.09 for 10,000-piece quantities. Motorola also offers an evaluation module including an MC33794, a Motorola 68HC908GR8 8-bit MCU, supporting components and RS232 communications port with necessary driver software. The evaluation module is available at the time of this writing for about $70.

As contemplated, some embodiments of the electrode assemblies are configured as an ad hoc network. For example, in an embodiment for deployment at a building structure having a scale of approximately 20 m by 20 m, it is assumed for purposes of illustration that one electrode per meter is placed along the exterior perimeter. This implies a network of 80 sensors, which produce 3,160 independent measurements per polling sequence—or about 32,000 measurement cycles per second. An eight-bit word would provide adequate resolution for measurements of electric potential, but for this illustration the word length is doubled to 16 bits to permit electrode addressing, time stamping and parity. The network of electrodes would be polled at a rate faster than human motion, for example, at 10 Hz. This implies that the sensor sampling rate would be about 10 kHz to obtain about 10 measurements per polling cycle or 1600 bits per second (bps) per electrode. In addition to information going from the constellation of electrodes to a central processor, commands and other data would be going from the central processor to the electrodes. The total communication load of the network is estimated to not exceed 500 kilobps (kbps, 1 kbps=103 bps).

Overall, it is expected that many embodiments will likely benefit from enhancements in the performance of information processing technologies. For example, ClearSpeed Technology, Inc. of Los Gatos, Calif. recently announced the availability of a new chip, the CS301—a parallel processor capable of performing 25 gigaflops ($10^9$ floating point operations per second). An ordinary desktop PC outfitted with six PCI cards, each containing four of the CS301 chips, would perform at about 600 gigaflops. Company literature suggests the CS301 co-processor may be on the market within a year and cost about $2,500. The CS301 is also very low-power, operating at about 2 watts, which allows it to run off a laptop battery and which does not require special cooling.

Two electrode deployment options are considered for some embodiments; airborne sensors hosted on micro-UAVs or robotic platforms designed to scale the vertical walls of building structures of interest. While DARPA has equity in both deployment options, miniature robotic systems are believed to have the highest short-term application and lowest risk. Other electrode deployment options are considered for other embodiments, such as electrodes, sensing means, communication means and processing means integrated into articles of clothing that can be worn by the warfighter in military applications, and by firefighters and other first responders in other situations.

Vertically climbing robotic platforms, such as the LEMUR are objects of current research and have been investigated by DARPA under the Controlled Biological Systems and Distributed Robotic Program. In some embodiments, miniature robotic systems are tethered for data transfer, control, power and a common electrical ground reference point. Hard wire tethers limits flexibility in some operational scenarios but also provides greater information assurance and higher accuracy (as noise due to variable ground reference is eliminated). In some embodiments, the wall scaling robotic systems are tethered to ground for a common reference, but communicate with the central processor and each other over low bandwidth, short range wireless communication links such as BLUETOOTH.

Airborne platforms such as the 24-inch diameter iSTAR Scaleable VTOL UAV System developed by DARPA have the advantage of mobility and the ease of deployment and are anticipated to be employed in some embodiments. The iSTAR UAV has a payload capacity of 20 pounds and a mission endurance of about 2 hours. In some embodiments, electrode assembly equipped iSTAR vehicles are deployed and aggregate around a building of interest. As the iSTAR is capable of extended hover operations, the electrode net could be simultaneously incremented to the next level of the building structure, producing a floor-by-floor map of interstitial dielectrics, with identification of probable humans. Signal gradients from emissions near walls provide an effective common electrical ground for all the sensors in the network. Such embodiments are anticipated to be engineered to deal with gradients near walls that might otherwise overwhelm the response signal and to deal with electrical noise induced by the propulsion engine.

Related to the choice of a deployment scheme are methods for exploiting electrode mobility as a resource to optimize the performance of the network, as described above.

4. Processor Hardware Overview

Figure 7:
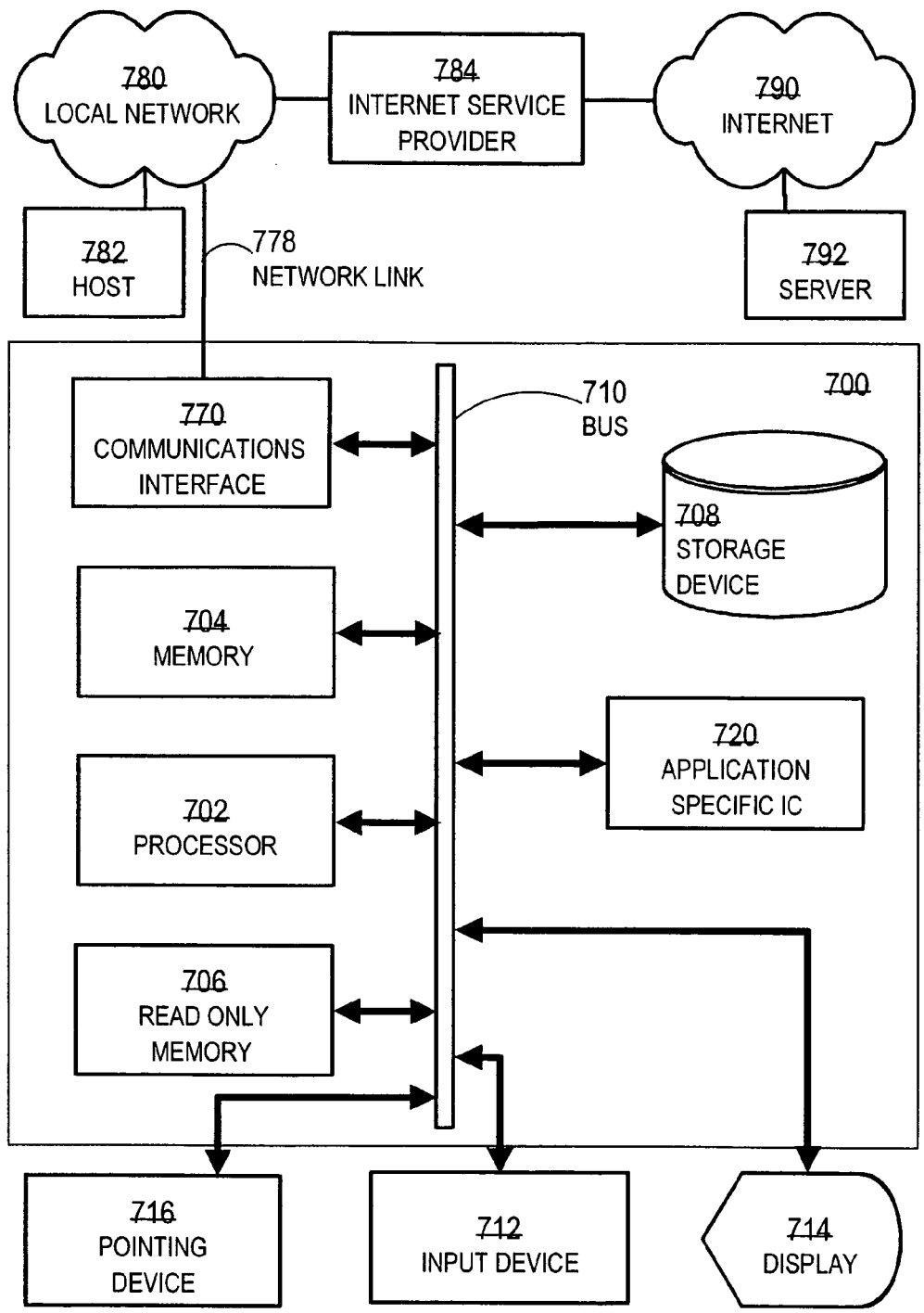
FIG. 7 is a block diagram that illustrates a computer system upon which an embodiment of the invention may be implemented and which may serve, in some embodiments, as the processor in an electrode assembly and a central unit.

FIG. 7 is a block diagram that illustrates a computer system 700 upon which an embodiment of the invention may be implemented and which may serve, in some embodiments, as the processor in an electrode assembly or a central unit or both. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular and atomic interactions. For example, north and south magnetic fields, or a zero and non-zero electric voltage, represent two states (0, 1) of a binary digit (bit). A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitute computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. For wireless links, the communications interface 770 sends and receives electrical, acoustic or electromagnetic signals, including infrared and optical signals, which carry information streams, such as digital data. Such signals are examples of carrier waves.

The term computer-readable medium is used herein to refer to any medium that participates in providing instructions to processor 702 for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, which carry information to and from computer system 700, are exemplary forms of carrier waves. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to an infra-red signal, a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for mapping dielectric objects in a building scale search region, comprising:
    (a) positioning a a three-dimensional array of electrodes to bound the search region;
    (b) driving particular electrodes in a defined sequence with signals having predetermined wavelengths longer than a dimension of the search region;
    (c) measuring resulting electric fields using one or more of the electrodes not being driven;
    (d) determining, based on fields measured, a three or quasi two-dimensional map of complex permitivities in the search region; and
    (e) from the three or quasi two-dimensional map of dielectric permitivities in the search area, creating a three or quasi two-dimensional map of objects in the search region.

2. The method of claim 1, wherein the predetermined wavelengths are longer than about one hundred meters.

3. The method of claim 1, wherein a particular electrode is driven to produce an electric field at a first time and is used to measure an electric field at a second time.

4. The method of claim 1, wherein:
    step (b) comprises producing electric fields at each of a plurality of frequencies; and
    step (d) comprises determining a dielectric map as a function of alternating current frequency of an induced field.

5. The method of claim 4, wherein step (d) comprises:
    (e) distinguishing a biological object from a non-biological object based at least in part on reconstruction and/or direct measurements of the frequency dependent complex permittivity.

6. The method of claim 1, wherein step (d) comprises determining at least one of:
    a complex permitivity of the dielectric object;
    a position of the dielectric object within the search region;
    a size of the dielectric object;
    an elongation of the dielectric object;
    an orientation of the dielectric object when it has an elongated shape; and
    a spectrally dependent complex permitivity of the dielectric object.

7. The method of claim 1, further comprising:
(e) associating a complex permitivity of the dielectric object with a biological entity.

8. The method of claim 1, wherein step (a) comprises positioning the plurality of electrodes so that they are separated from dielectric objects using a blocking material having differentiable complex permittivity.

9. The method of claim 8, wherein the blocking material is visually opaque.

10. The method of claim 8, wherein step (a) comprises positioning the plurality of electrodes so that they are not in physical contact with the blocking material.

11. The method of claim 8, further comprising embedding one or more blocking materials with conducting sub structures.

12. The method of claim 1, wherein step (a) comprises adaptively repositioning at least one electrode to optimize performance of step (d).

13. The method of claim 1, wherein step (a) comprises positioning at least one electrode with respect to a second electrode to optimize performance of step (d).

14. The method of claim 1, wherein step (a) comprises positioning a first electrode so that is spaced more than about five meters from a second electrode.

15. The method of claim 1, further comprising:
(e) excluding a first particular electrode of the plurality of electrodes from measuring during production of a particular electric field by a second particular electrode of the plurality of the electrodes.

16. The method of claim 15, wherein step (e) performs the excluding to optimize performance of step (d).

17. The method of claim 1, wherein step (b) comprises producing an electric field using only one electrode at a time.

18. The method of claim 1, wherein step (b) comprises:
determining a particular temporal and spatial sequence for driving electrodes of the plurality of electrodes to optimize step (d); and
producing electric fields using electrodes of the plurality of electrodes in the particular temporal and spatial sequence.

19. The method of claim 1, wherein step (c) comprises using a particular electrode to measure that is also driven to produce an electric field.

20. The method of claim 1, wherein step (c) comprises measuring an electrical potential of the electric field at an electrode of the plurality of electrodes.

21. The method of claim 1, wherein step (c) comprises measuring a current induced by the electric field at an electrode of the plurality of electrodes.

22. The method of claim 1, wherein step (c) comprises measuring an associated magnetic field at an electrode of the plurality of electrodes.

23. The method of claim 1, wherein step (d) comprises modeling based on inversion including performing a forward computation that includes representing the dielectric object as an object that allows an analytical solution for the property of the electric field at an electrode of the plurality of electrodes.

24. The method of claim 1, wherein:
step (b) comprises (b1) producing a first electric field using a first electrode of the plurality of electrodes and (b2) producing a second electric field using a second electrode of the plurality of electrodes after producing the first electric field; and
step (a) comprises positioning the electrode after step (b1) and before step (b2).

25. The method of claim 24, further comprising:
(e) determining a position change for an electrode with respect to a different electrode based on measuring a first electric field using a first subset of the plurality of electrodes, wherein step (a) comprises repositioning the electrode according to the position change.

26. The method of claim 25, wherein step (e) comprises determining the position change to optimize step (d).

27. The method of claim 24, wherein the first emitter electrode is the same as the second emitter electrode.

28. The method of claim 24 wherein the first electrode is different from the second electrode.

29. The method of claim 1, wherein step (b) comprises emitting one or more temporal pulses of an electric field, each pulse comprising a combination of a plurality of wavelengths, each wavelength being longer than about one hundred meters.

* * * * *

UNITED STATES PATENT AND TRADEMARK OFFICE
CERTIFICATE OF CORRECTION

PATENT NO. : 7,330,032 B2 Page 1 of 1
APPLICATION NO. : 10/993421
DATED : February 12, 2008
INVENTOR(S) : Nicholas C. Donnangelo It is certified that error appears in the above-identified patent and that said Letters Patent is hereby corrected as shown below:

Column 13
Line 20 "surveillance finction" replace with --surveillance function--.

Column 46
Line 27 "positioning a a three-dimensional" replace with --positioning a three-dimensional--.
Line 35 "permitivities" replace with --permittivities--.
Line 38 "permitivities" replace with --permittivities--.
Line 60 "permitivity" replace with --permittivity--.
Line 66 "permitivity" replace with --permittivity--.

Column 47
Line 2 "permitivity" replace with --permittivity--.
Line 23 "first electrode so that is spaced" replace with --first electrode so that said first electrode is spaced--.
Line 29 "plurality of the electrodes" replace with --plurality of electrodes--.

Signed and Sealed this

Tenth Day of June, 2008

JON W. DUDAS
*Director of the United States Patent and Trademark Office*